US009694169B2

(12) United States Patent
Serpe

(10) Patent No.: US 9,694,169 B2
(45) Date of Patent: Jul. 4, 2017

(54) GEL ASSEMBLY

(71) Applicant: Governors of the University of Alberta, Edmonton (CA)

(72) Inventor: Michael J. Serpe, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 1246 days.

(21) Appl. No.: 13/662,117

(22) Filed: Oct. 26, 2012

(65) Prior Publication Data
US 2013/0110040 A1    May 2, 2013

Related U.S. Application Data

(60) Provisional application No. 61/551,882, filed on Oct. 26, 2011.

(51) Int. Cl.
*A61M 37/00* (2006.01)
*B32B 15/08* (2006.01)
*A61K 41/00* (2006.01)
*A61K 9/70* (2006.01)

(52) U.S. Cl.
CPC ......... *A61M 37/00* (2013.01); *A61K 41/0028* (2013.01); *B32B 15/08* (2013.01); *A61K 9/7007* (2013.01); *Y10T 428/24942* (2015.01); *Y10T 428/24975* (2015.01); *Y10T 428/254* (2015.01); *Y10T 428/31678* (2015.04); *Y10T 428/31692* (2015.04)

(58) Field of Classification Search
CPC ............ A61K 41/0028; Y10T 428/254; Y10T 428/31678
See application file for complete search history.

(56) References Cited

U.S. PATENT DOCUMENTS

| 2,806,509 A * | 9/1957 | Sheatsley | ................ B29C 70/02 109/80 |
| 5,150,236 A | 9/1992 | Patel | |
| 5,672,297 A * | 9/1997 | Soane | ...................... H01B 1/20 252/500 |
| 2005/0047968 A1* | 3/2005 | Kido | ................... B01L 3/50273 422/400 |
| 2005/0104049 A1* | 5/2005 | Tsutsui | ..................... G02F 1/17 252/583 |
| 2005/0196532 A1* | 9/2005 | Waldrop, III | ........ G01N 29/036 427/240 |
| 2006/0121285 A1* | 6/2006 | Nakayama | ............ G02F 1/0121 428/411.1 |
| 2006/0261252 A1* | 11/2006 | Cole | ........................ G01J 3/02 250/214.1 |
| 2007/0248987 A1 | 10/2007 | Imamura et al. | |
| 2008/0013159 A1* | 1/2008 | Fallahi | ................... G02F 1/061 359/321 |
| 2008/0187655 A1* | 8/2008 | Markle | .............. G01N 21/7703 427/154 |
| 2008/0241214 A1* | 10/2008 | Myung | ................... A61L 27/06 424/423 |
| 2008/0291424 A1* | 11/2008 | Lei | .......................... B01L 3/508 356/445 |
| 2009/0156917 A1* | 6/2009 | Martini | ............. A61B 5/14532 600/341 |
| 2010/0049015 A1* | 2/2010 | Martini | ............. A61B 5/14532 600/310 |
| 2010/0209698 A1* | 8/2010 | Kornherr | ................ B41M 5/26 428/323 |
| 2016/0033389 A1 | 2/2016 | Serpe | |

FOREIGN PATENT DOCUMENTS

EP      0568943 A1 * 11/1993 ............... F21V 7/22

OTHER PUBLICATIONS

Sorrell et al. "Reflection Order Selectivity of Color Tunable Poly(N-isopropylacrylamide Microgel Based Etalons", Adv. Mater. 2011, 23, 4088-4092.*
Buschow et al., "Hydrogels", Encyclopedia of Materials-Science and Technology, vol. 1-11, Elsevier, Online version available at: http://app.knovel.com/hotlink/toc/id:kpEMSTV001/encyclopedia-materials/encyclopedia-materials, 2001, p. 3878.*
Gan et al. "Low drive voltage Fabry-Perot etalon device tunable filters using poled hybrid sol-gel materials", Applied Physics Letters, 89, 2006, 041127-1 to 041127-3.*
Ashkenazi et al. "High frequency ultrasound imaging using Fabry-Perot optical etalon", Medical Imaging 2005:Ultrasonic Imaging and Signal Processing, pp. 289-297.*
Chang et al. "Polymer gel light-emitting devices", Applied Physics Letters, 75, 1999, 2713-2715.*
Courtney D. Sorrell, Michael J. Serpe: "Glucose Sensitive Poly (N-isopropylacrylamide) Microgel Based Etalons", Anal Bioanal Chem (2012) 402:2385-2393.
Liang Hu, Michael J. Serpe:"Color Modulation of Spatially Isolated Regions on a Single Poly(N-isopropylacrylamide) Microgel Based Etalon"; Journal of Materials Chemistry; 2012, 22; p. 8199-8202.
Johnson et al; Detecting Solution pH Changes Using Poly (N-isopropylacrylamide)-Co-Acrylic Acid Microgel-Based Etalon Modified Quartz Crystal Microbalances; Analytica Chimica Acta 739; 2012; p. 83-88.
Liang Hu, Michael J. Serpe: Color-Tunable Etalons Assembled From Poly (N-isopropylacrylamide) Based Microgels; Polymers; 2012; 4, p. 134-149.
Courtney D. Sorrell; Michael J. Serpe: "Reflection Order Selectivity of Color-Tunable Poly (N-isopropylacrylamide) Microgel Based Etalons"; Paper submitted to Advanced Materials;.

(Continued)

*Primary Examiner* — Nicole M Buie-Hatcher
(74) *Attorney, Agent, or Firm* — Anthony R. Lambert

(57) ABSTRACT

A gel assembly comprising a polymeric gel layer between metal layers. A gel assembly process comprising providing a colloidal polymer in solution, drying the solution to form a polymeric gel layer and forming metal layers on either side of the polymeric gel layer. A method of drug delivery comprising loading a polymeric gel layer with drug, forming metal layers on either side of the polymeric gel layer, wherein the polymeric gel layer comprises a material that is sensitive to a stimulus, and subjecting the polymeric gel layer to the stimulus to release the drug from between or through the metal layers.

3 Claims, 11 Drawing Sheets

(56) References Cited

OTHER PUBLICATIONS

Sorrell et al. "A "Paint-On" Protocol for the Facile Assembly of Uniform Microgel Coatings for Color Tunable Etalon Fabrication"; American Chemical Society Mater. Interfaces; 2011, 3, p. 1140-1147.

B.J. Worfolk et al. "Self-Assembly of Polymer Nanowires for Efficient Plastic Solar Cells"; Affiches Conference 2012; downloaded from www.nanoquebec.ca/media/affiches-conference-nq-2012.

Minghong Yang et al."Optical Fiber Sensors With Fabry-Perot Thin Film Coating as Sensitive Element"; Paper from the 5th International Symposium on Advanced Optical Manufacturing and Testing Technologies, Proc of SPIE; vol. 7659; 2010; p. 1-5.

Xiaobing Li et al.; "Optical Fiber Humidity Sensor With PVDF Thin Film as Sensitive Element"; Proc of SPIE, vol. 7853; p. 1-5.

Matthew C.D. Carter et al.; "Deswelling Kinetics of Color Tunable Poly N-isopropylacrylamide) Microgel-Based Etalons"; The Journal of Physical Chemistry B; 2011; 115; p. 14359-14368.

Courtney D. Sorrell et al. Color Tunable Poly (N-isopropylacrylamide)-Co-Acrylic Acid Microgel-Au Hybrid Assemblies; Advanced Functional Materials; 2011, 21, p. 425-433.

Lian Hu and Michael J. Serpe; Poly (N-isopropylacrylamide) Microgel-Based Etalons for Optical Sensing; J. Anal Bioanal Techniques; 2012, vol. 3, issue 2; p. 1-4.

Courtney D. Sorrell et al. Color Tunable Poly (N-isopropylacrylamide)-Co-Acrylic Acid Microget/Au Hybrid Assemblies; Paper submitted to Advanced Materials.

T. P. Russell, Surface-responsive materials, Science 2002, 297, 964.

M. J. Serpe, K. A. Yarmey, C. M. Nolan, L A. Lyon, Doxorubicin uptake and release from microgel thin films, Biomacromolecules 2005, 6, 408.

Hoare, T.; Pelton, R. Macromolecules 2004, 37, 2544-2550.

\* cited by examiner

GEL ASSEMBLY

CROSS-REFERENCE TO RELATED APPLICATIONS

This application claims the benefit under 35 USC 119(e) of U.S. provisional application no. 61/551,882 filed Oct. 26, 2011, the content of which is hereby incorporated by reference in its entirety.

FIELD

Functional optical and drug dispensing materials.

BACKGROUND

Functional optical materials have utility in lasers, electronics, sensors, smart medical devices, point of care medical diagnostic devices, environmentally friendly coatings, switchable displays, forgery detection and other technologies. Various approaches have been disclosed in articles cited in Sorrell, C. D. et al., 2011, Color Tunable Poly (N-Isopropylacrylamide)-co-Acrylic Acid Microgel/Au Hybrid Assemblies, Adv. Funct. Mater. 21: 425-433; Sorrell, C. D., et al., 2011, Reflection order selectivity of color-tunable poly (N-isopropylacrylamide) microgel based etalons, Adv. Mater. 23:4088-4092; Sorrell, C. D., et al., 2011, A "Paint-On" Protocol for the Facile Assembly of Uniform Microgel Coatings for Color Tunable Etalon Fabrication, ACS Appl. Mater. Interf. 3: 1140-1147; Sorrell, C.D., et al., 2012, Glucose Sensitive Poly (N-Isopropylacrylamide) Microgel Based Etalons, Anal. Bioanal. Chem. 402:2385-2393; Hu, L., et al.,2012, Color Modulation of Spatially Isolated Regions on a Single Poly (N-isopropylacrylamide) Microgel Based Etalon, J. Mater. Chem. 22:8199-8202; Johnson, K.C.C., et al., 2012, Detecting Solution pH Changes Using Poly (N-Isopropylacrylamide)-co-Acrylic Acid Microgel-Based Etalon Modified Quartz Crystal Microbalances, Anal. Chim. Atca 739:83-88; Carter, M. C. D., et al., 2011, Deswelling Kinetics of Color Tunable poly (N-isopropylacrylamide) Microgel-based Etalons, J. Phys. Chem. B 115:14359-14368; Hu, L., et al., 2012, Poly (N-Isopropylacrylamide) Microgel-Based Etalons for Optical Sensing, J. Anal. Bioanal. Techniques 3:2; Hu, L., et al., 2012, Color-Tunable Etalons Assembled from Poly (N-Isopropylacrylamide) Based Microgels, Polymers 4:134-149 and elsewhere. The inventor provides a new class of functional optical materials for use in these and other applications. Each of these articles and their supplemental materials is incorporated by reference herein in its entirety.

SUMMARY

In an embodiment, there is disclosed a gel assembly comprising a polymeric gel layer between metal layers. In another embodiment, there is disclosed a gel assembly process comprising providing a colloidal polymer in solution, drying the solution to form a polymeric gel layer and forming metal layers on either side of the polymeric gel layer. In a further embodiment, there is disclosed a method of drug delivery comprising loading a polymeric gel layer with drug, forming metal layers on either side of the polymeric gel layer, and wherein the polymeric gel layer comprises a material that is sensitive to a stimulus, and subjecting the polymeric gel layer to the stimulus to release the drug from between or through the metal layers.

One or more further features following may be combined with these embodiments: the polymeric gel layer comprises at least a monomer having at least an atom with a free electron pair per monomer unit; the atom with a free electron pair comprises one or more of nitrogen, fluorine, chlorine, or phosphorus atoms; in which the metal layers are reflective; the metal layers are parallel to each other; the metal layers are sufficiently thin to be transparent; the gel assembly is formed as an etalon in which the metal layers have a different refractive index from the polymeric gel layer; the polymeric gel layer comprises a stimulus responsive material that changes volume in response to a stimulus; the stimulus responsive material comprises one or more of thermoresponsive polymers, pH responsive polymers, electroresponsive polymers, hydrophilic polymers, magnetoresponsive polymers, chemical responsive polymers, ionic strength responsive polymers and photoresponsive polymers; the polymeric gel layer is formed as a colloidal gel; the colloidal gel comprises packed particles, the particles having an unstressed diameter and as packed particles having a center to center particle distance that is smaller than the unstressed diameter; the polymeric gel layer comprises a co-polymer formed of one or more co-monomers in addition to the monomer; a monomer with at least one nitrogen, fluorine, chlorine, or phosphorus per monomer unit is the main monomer in the co-polymer; some monomers in the co-polymer are individually non-responsive to a stimulus or one or more of the co-monomers are responsive to more than one stimulus or the co-polymer comprises monomers that are responsive to different stimuli; the polymeric gel layer comprises colloidal particles having an effective diameter between 0.05 micron and 250 microns; the metal layers are formed as coatings on the polymeric gel layer; the polymeric gel layer is loaded with drug; the metal layers or at least one of the metal layers are less than 10 nm thick, or less than 20, 40, 60, 80 or 100 nm thick; the gel assembly is incorporated into a microbalance; and the polymeric gel layer comprises a glucose sensitive polymer.

BRIEF DESCIPTION OF THE DRAWINGS

There will now be described embodiments of the invention with reference to the drawings by way of example, in which:

FIG. 1 shows (paper A FIG. 1) SEM images (with photograph inset) of microgel films deposited from, in part a, water and in part b, buffer and after addition of a Au overlayer to the film deposited from, in part c,water, and in part b, buffer. Part e shows a SEM image (with photograph inset) for a microgel film deposited from water on glass with a Au/microgel/Au overlayer. The surfaces were scratched with a razor to give SEM image contrast between the microgels and the surface, and to show film structure. For parts a-d the images were collected at 85° relative to the surface normal using an accelerating voltage of 20 kV, while the image in part e was collected at 50° relative to the surface normal with an accelerating voltage of 5 kV. Scale bars are 1 μm for SEM images, and ~2 mm for photograph insets.

FIG. 2 shows (paper A FIG. 5.) (top) AFM images for microgel etalons in pH 3.0 water at, in part a, 25° C., in part b, after the temperature was increased to 40° C., and, in part c, after it was cooled again to 25° C. The surface was scratched to give contrast between the film and the surface, and the height determined from two points along a line profile (bottom, solid line) averaged over 100 vertical points (boundaries marked by dashed lines in images). The analyses revealed that the heights were in part a, 948 nm±42 nm, in part b, 565 nm±15 nm, and in part c, 955 nm±27 nm. The RMS roughness of part a is 110 nm, and part b is 113 nm. Scale bars are 10 μm.

Figure 7:
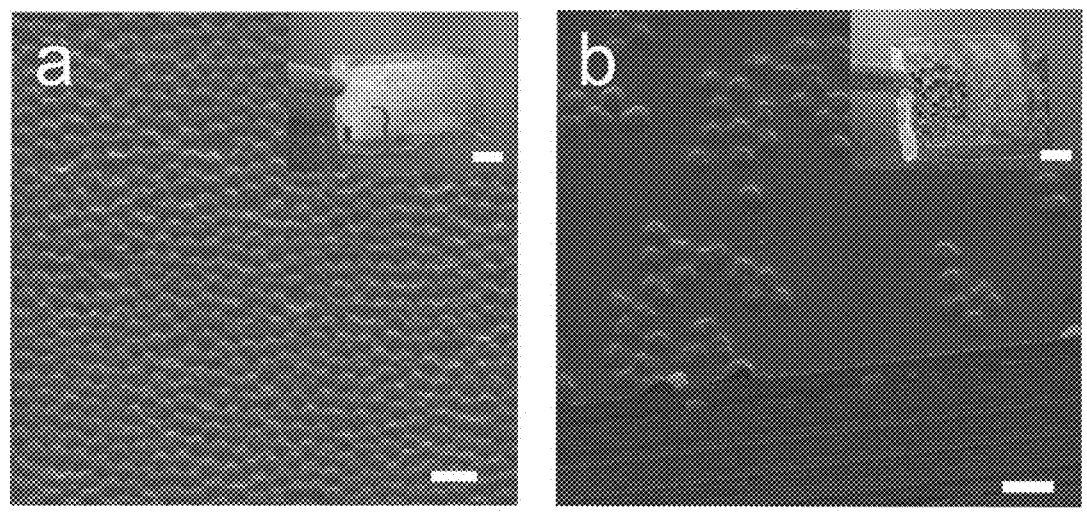

FIG. 7 shows (paper A Figure SI 5) SEM images (photograph inset) for a microgel etalon deposited from, in part a, water and in part b, buffer after heating in pH 3.0 and pH 6.5. SEM image was collected 30° relative to the surface normal. The Au under and overlayer can be clearly seen in part b. Scale bars for SEM images are 2 μm, and for the photograph are 2 mm.

Figure 8:
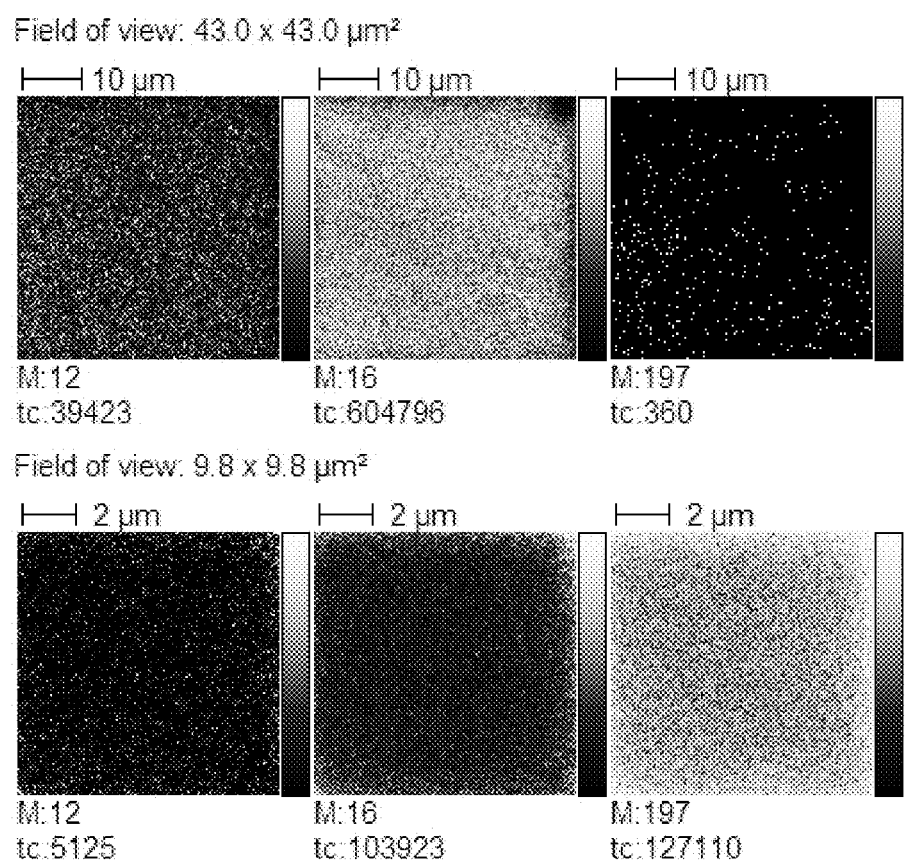

FIG. 8 shows (paper A Figure SI 6) Secondary ion mass spectrometry (SIMS) images for a Au substrate coated with microgels deposited from water (top) without, and (bottom) with a Au overlayer. These images were collected after heating in pH 3.0 and 6.5 solution. M:12=C, M:16=O, M:197=Au. Dark colors indicate low signal, while light color indicates high signal (also low tc values correspond to low signal and high tc values correspond to high signal). These images show that the Au overlayer completely coats the microgel layer.

Figure 9:
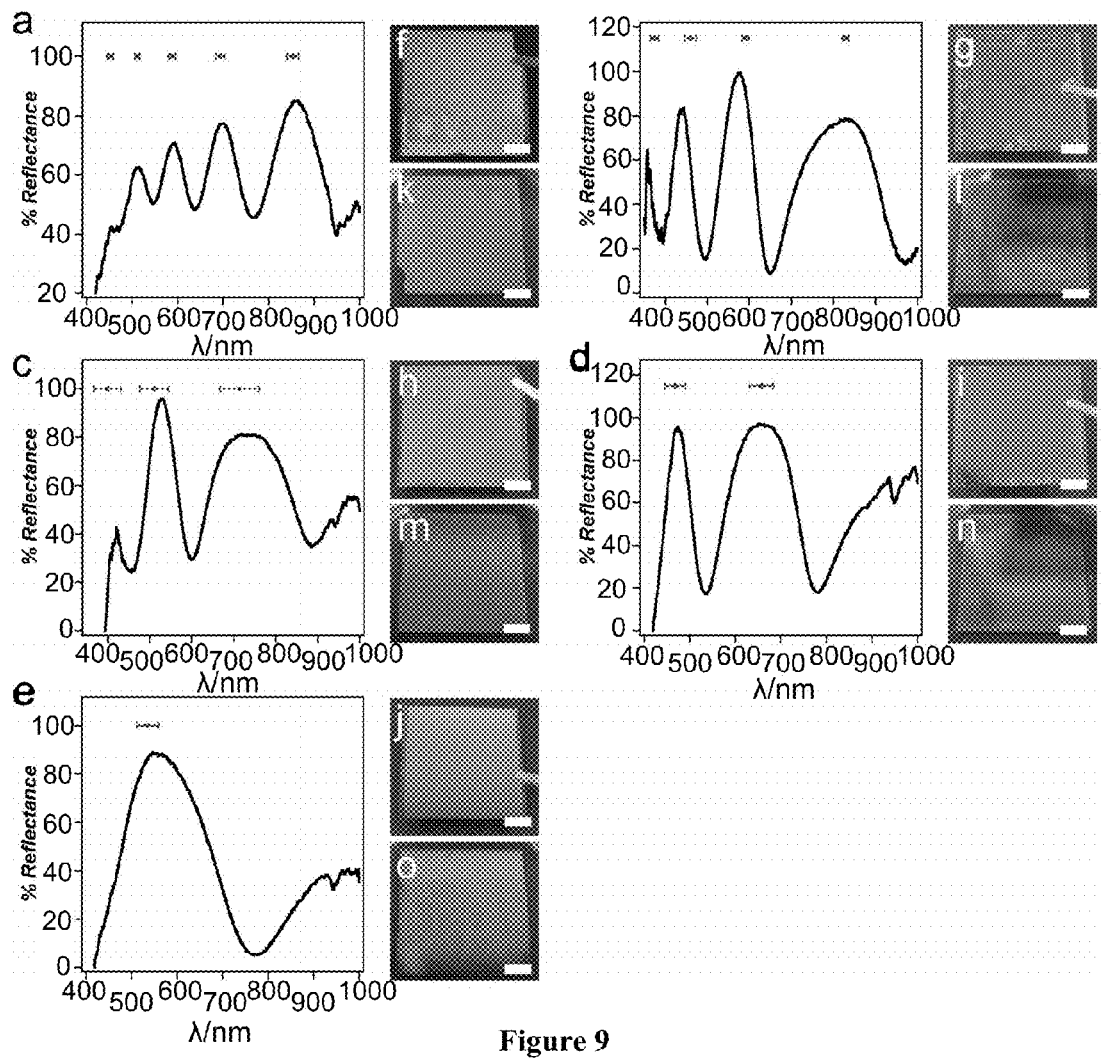
Figure 10:
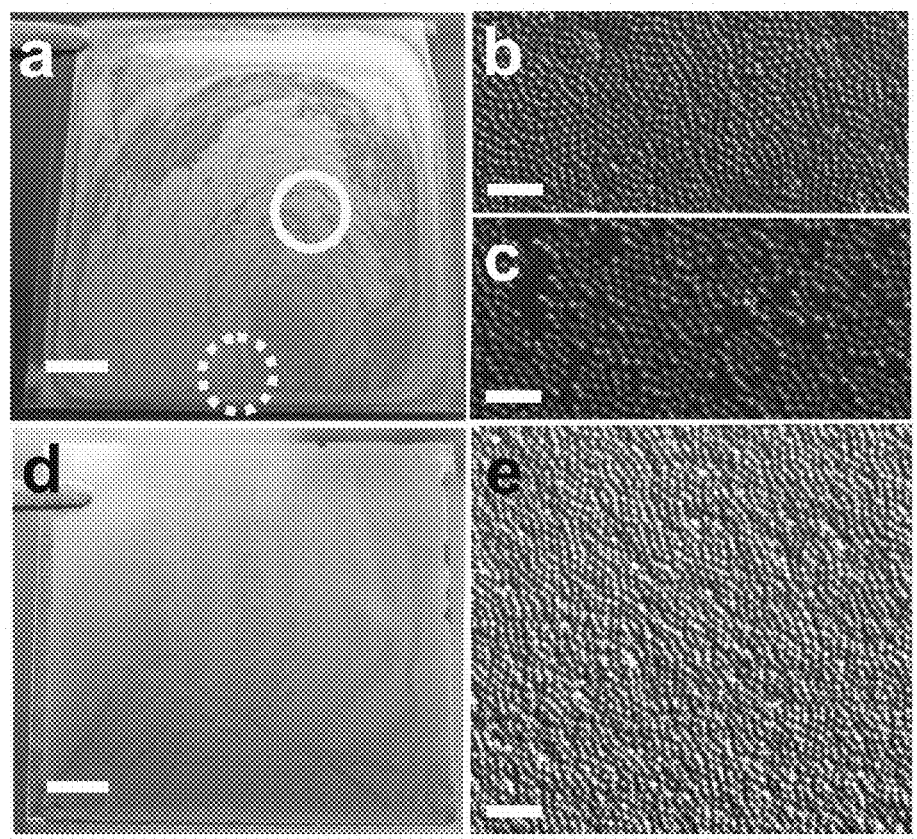

FIG. 9 shows (paper B FIG. 1) Representative spectra for etalons composed of: in part a, pNIPAm-co-AAc-1, in part b, pNIPAm-co-AAm, in part c, pNIPAm-co-AAc-2, in part d, pNIPAm-co-VAA, in part e, pNIPAm-co-AAc-3 microgels, obtained in pH 3 formate buffer. The average peak position (±one standard deviation) from six spectra is shown in red above each spectrum (data provided in Table 1). Parts f-j show photographs for the etalons in parts a-e in the dry state, respectively; parts k-o show photographs for the etalons in parts a-e hydrated in pH 3 formate buffer, respectively. Scale bars for photographs are 5 mm FIG. 10 shows (paper C FIG. 1) Photographs and DIC microscopy images showing microgel films fabricated from the two methods described. Part a shows the photograph of an etalon made by our previously used drying method, and the corresponding DIC microscopy images of part b, an area which is an etalon, and part c, an area which is not an etalon. The microscopy images were taken before Au coating in regions approximated by the white circles on the photograph in part a. The solid white circle corresponds with part b, and the dashed white circle corresponds with part c. Part d shows a photograph of an etalon made by the presented "paint-on" method, and part e shows the corresponding DIC microscopy image before Au coating to make the etalon in part d. The microgel coverage was uniform across the whole surface area of the substrate. The photographs were taken with an Olympus C-7070 Wide Zoom digital camera, after the addition of a 2 nm Cr and 15 nm Au layer on top of the microgels as an overlayer. DIC microscopy images were obtained before Au overlayer addition with a 100x oil immersion objective. Scale bars are 5 mm for the photographs, and 5 μm for the micrographs.

Figure 11:
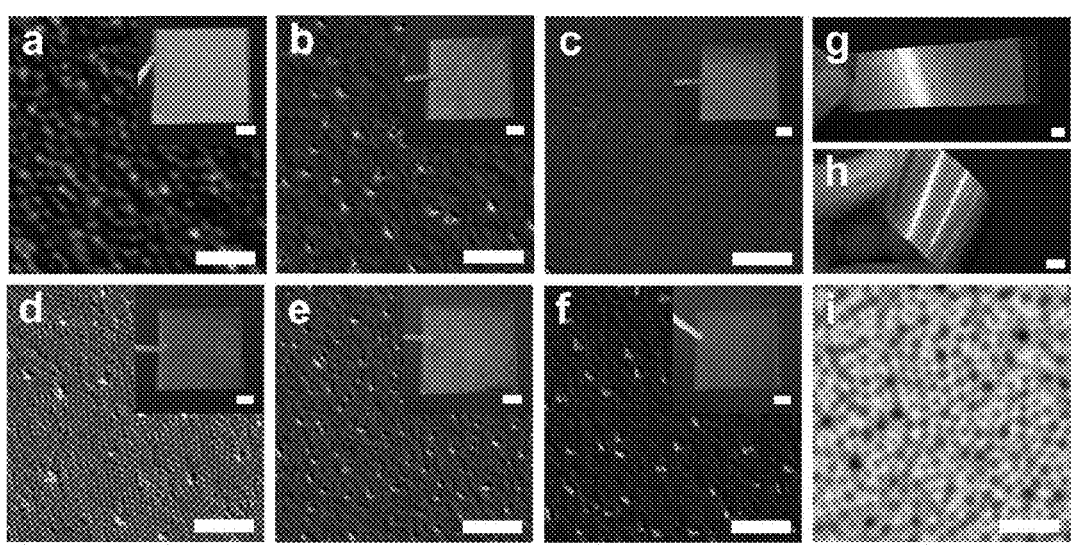

FIG. 11 shows (paper C FIG. 3) DIC microscopy images and photographs (insets) showing films made from, in part a, pNIPAm-co-AAc-1 microgels, in part b, pNIPAm-co-AAc-2 microgels, in part c, pNIPAm-co-AAc-3 microgels, in part d, pNIPAm-BIS microgels, in part e, pNIPAm-co-AAm microgels, and in part f, pNIPAm-co-VAA microgels. Photographs of an etalon generated from pNIPAm-co-AAc-1 microgels deposited on a flexible surface, unbent in part g and bent in part h, and a DIC micrograph of the microgel film on the flexible substrate in part i. Scale bars are 5 μm and 5 mm for the micrographs and photographs, respectively. All DIC images were taken before the addition of the Cr/Au overlayer; all photographs were taken after the addition of a Au overlayer using a Pentax K-2000 DSLR camera. The DIC image shown in part i was taken through a glass coverslip with the sample inverted on top in order to match the optical path required for the objective. All DIC images except part d were taken using a 1.6× magnification booster. The defects seen in parts b, d, e and f are features on the Cr/Au underlayer and we hypothesize that they formed during the Au evaporation and/or annealing processes. These features do not impact the optical properties or quality of etalons made via this technique.

Figure 1:
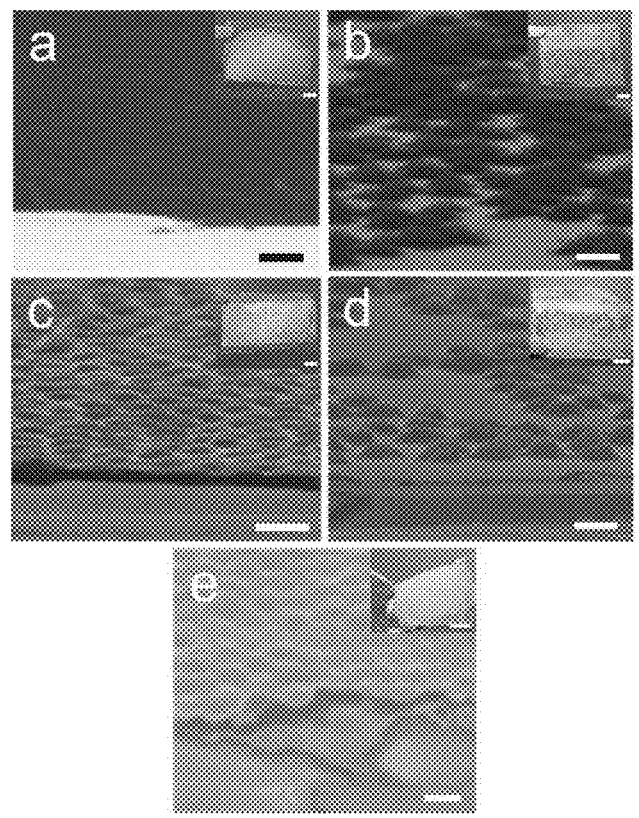
Figure 12:
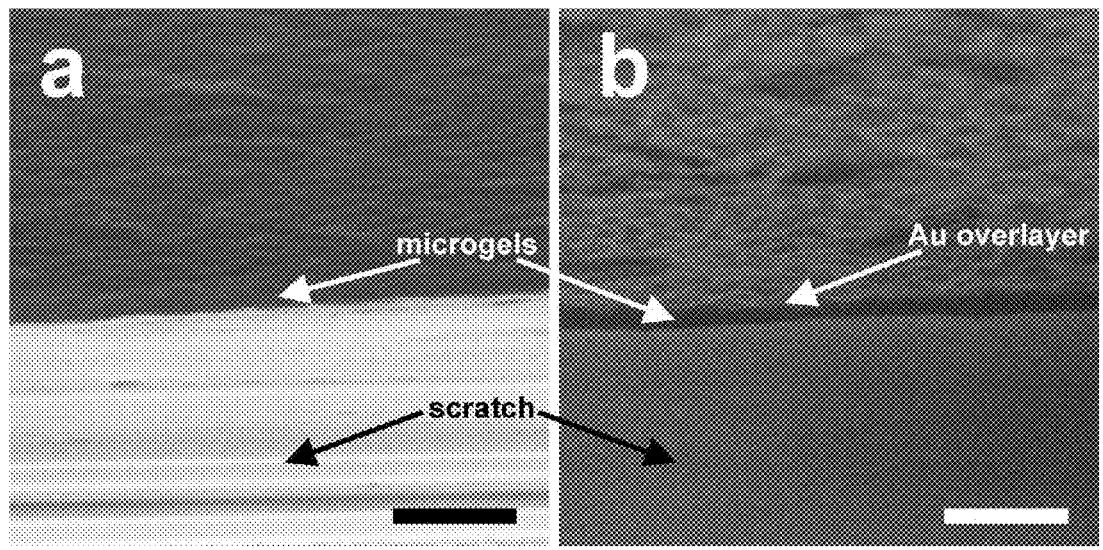

FIG. 12 shows (paper C SI FIG. 1.) SEM images for, in part a, a film made by the "paint-on" method with no Au overlayer, and, in part b, a film made by the "paint-on" method with a 2 nm Cr/15 nm Au overlayer. The film imaged in part b is the same film presented in FIG. 1 parts d and e. Scale bars are 2 μm. The images were acquired by scratching a region of the substrate with a razor blade and then imaging at an 80° angle to the surface normal.

Figure 13:
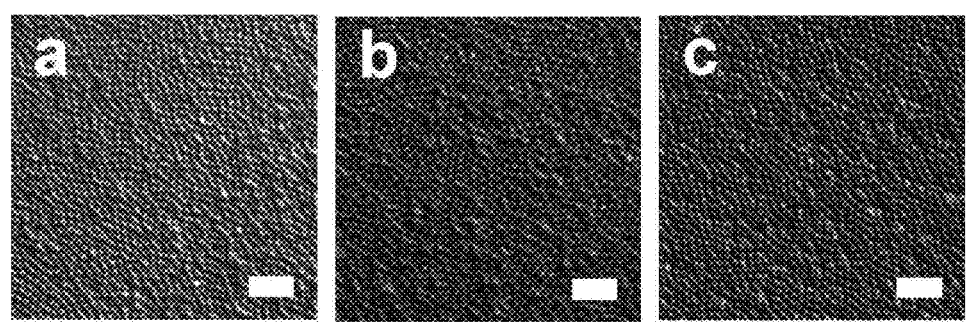

FIG. 13 shows (paper C SI FIG. 2) DIC microscopy images for microgel films painted on Au and soaked in D.I. water for, in part a 1 day, in part b 18 days, and in part c 48 days. Images show that there is no significant difference in particle density due to long-term soaking Scale bars are 5 μm.

Figure 14:
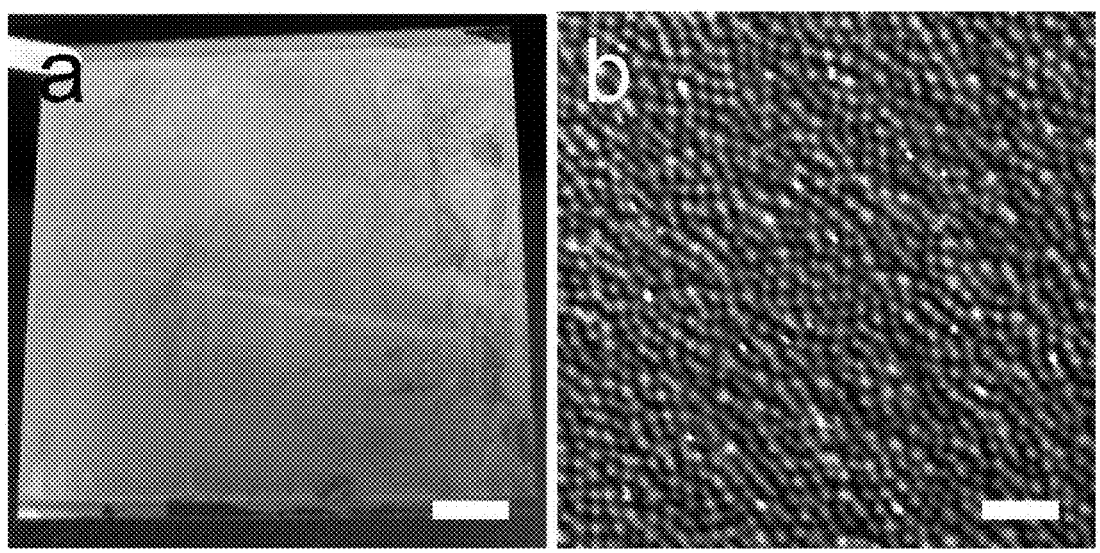

FIG. 14 shows (paper C SI FIG. 3.) a photograph in part a and DIC microscopy image in part b of a NIPAm-co-AAc-1 film painted at room temperature on a Au substrate. Images show that temperature control at 30° C. during deposition is not entirely necessary. Scale bars are 5 mm (photo) and 5 μm (DIC).

Figure 4:
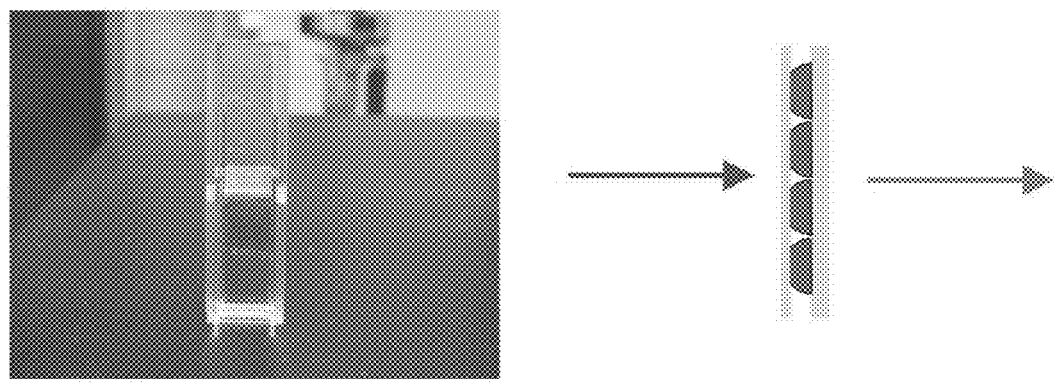
FIG. 4 shows (paper A Figure SI 2) (left) a photograph of the cuvette assembly used to study our thin films. The film is taped to the inside wall of the cuvette. (Right) Schematic of the light path for the experiment, i.e., light strikes the film at normal incidence and the transmitted light is collected. "Absorbance" of the film is actually due to reflectance.
Figure 15:
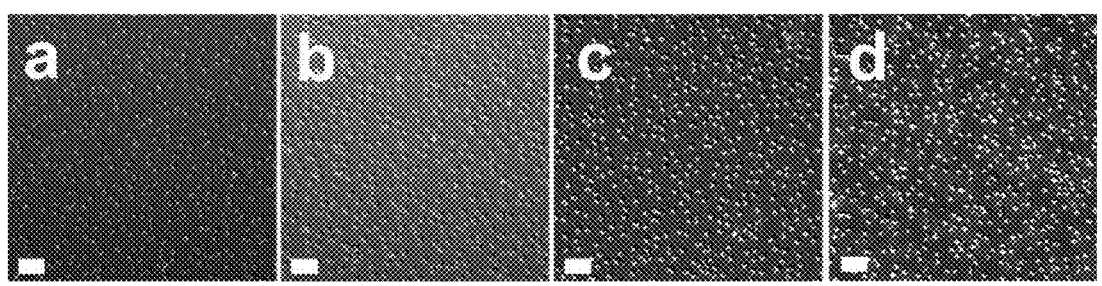

FIG. 15 shows (paper C SI FIG. 4.) DIC microscopy of Au substrates that were exposed to 775 μL of a 5% (v/v) microgel solution without drying (same conditions as used for the generation of etalons via the traditional drying protocol) for, in part a, 2 hours, in part b, 4 hours, in part c, 6 hours, and in part d, 8 hours. There is no significant additional adsorption of microgels beyond the 2-hour mark, which supports our hypothesis that drying is necessary to create monolithic films. All films were imaged using a 1.6× magnification booster. Scale bars are 5 μm.

Figure 5:
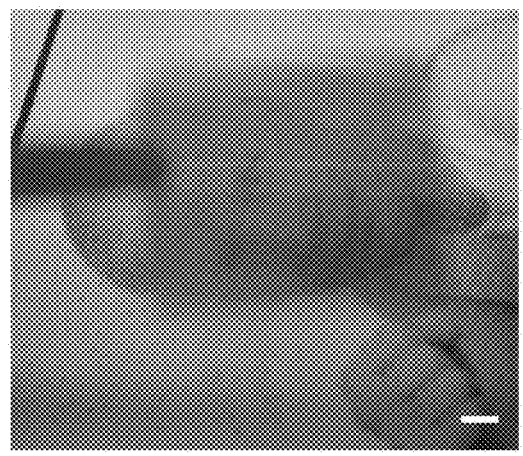
FIG. 5 shows (paper A Figure SI 3) a photograph of a picture through a typical etalon to show its transparency. The scale bar is 2 mm.
Figure 16:
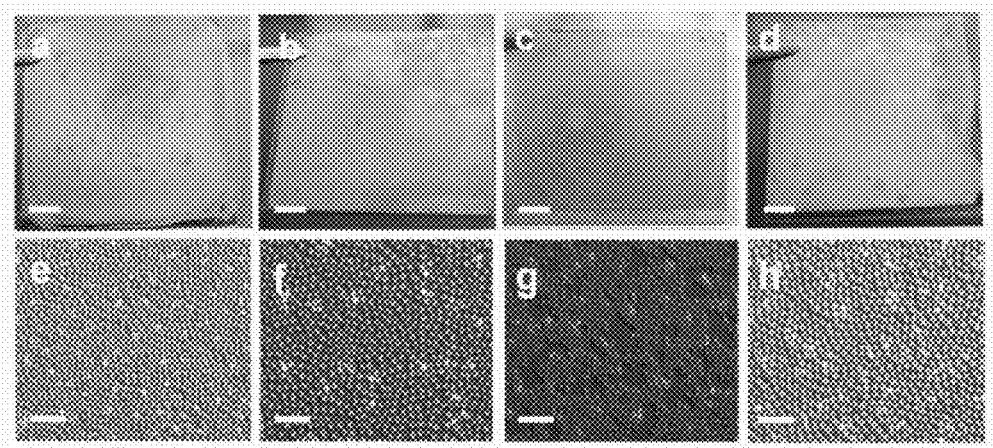

FIG. 16 shows (paper C SI SI FIG. 5.) Films made by modulating pH and ionic strength. Top: Photographs of films made by drying 5% (v/v) microgel solutions on Au coated substrates, in part a at pH 6.5, I.S.=1 mM, part b at pH 6.5, I.S. 100 mM, part c at pH 3.0, I.S. 1 mM, and part d at pH 3.0, I.S. 100 mM. All of the photographs were taken after the microgel film was coated with a 2 nm Cr and 15 nm Au overlayer using an Olympus C-7070 camera. Bottom: DIC microscopy images for the corresponding films above, before Au coating, in part e atpH 6.5, I.S.=1 mM, in part f at pH 6.5, I.S. 100 mM, in part g at pH 3.0, I.S. 1 mM, and in part h at pH 3.0, I.S. 100 mM. Scale bars are 5 mm for the photographs, and 5 μm for the micrographs. All images were taken using a 1.6× magnification booster.

Figure 6:
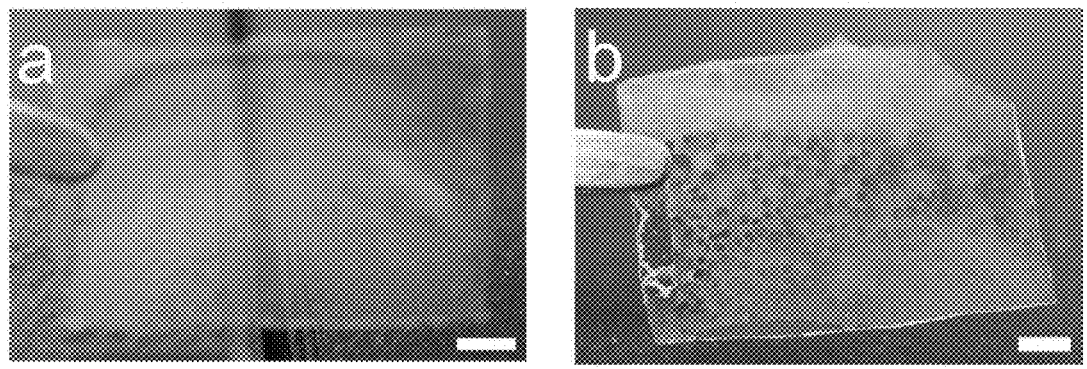
FIG. 6 shows (paper A Figure SI 4) photographs for a microgel film deposited on Au from, in part a, water, and in part b, buffer after heating in pH 3.0 and pH 6.5. Scale bars are 2 mm.
Figure 17:
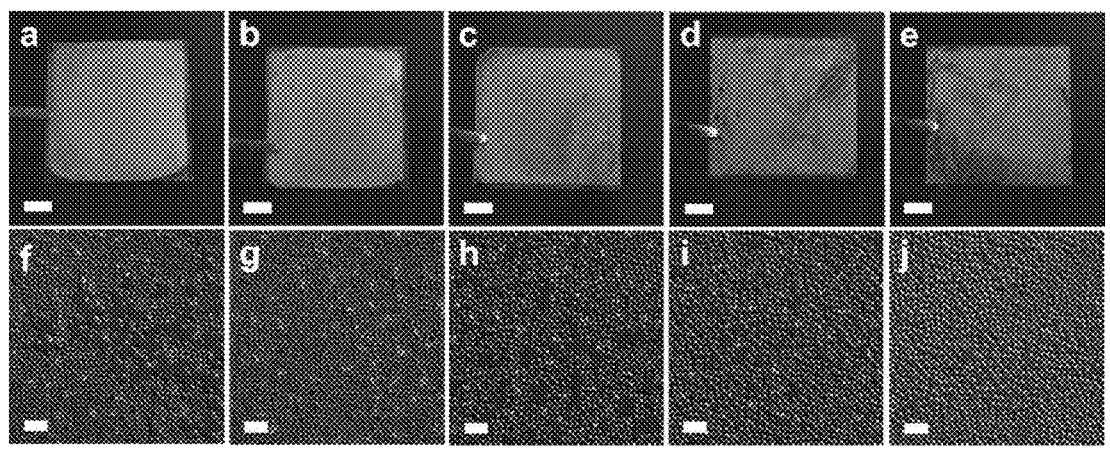

FIG. 17 shows (paper C SI FIG. 6.) Films made by drying with varying surfactant concentration. Top: Photographs of films made by drying 5% (v/v) microgel solutions with some added total w/v % of sodium dodecylsulfate (SDS) on Au coated substrates with, in part a 0.01 w/v %, in part b 0.05 w/v %, in part c 0.1 w/v %, in part d 0.5 w/v %, and in part e 1.0 w/v % SDS. All of the photographs were taken after the microgel film was coated with a 2 nm Cr and 15 nm Au overlayer using a Pentax K-2000 DSLR camera. Bottom: DIC microscopy images for the corresponding films above, before Au coating with, in part f 0.01 w/v %, in part g 0.05 w/v %, in part h 0.1 w/v %, in part i 0.5 w/v %, and in part j 1.0 w/v % SDS. Scale bars are 5 mm for the photographs, and 5 μm for the micrographs.

Figure 18:
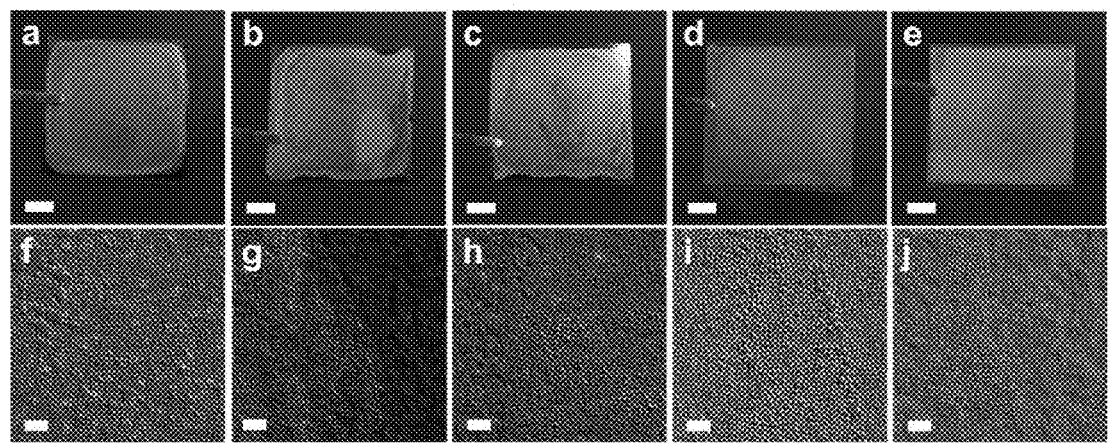

FIG. 18 shows (paper C SI FIG. 7.) Films made using a co-solvent mixture of water and ethanol. Top: Photographs of films made by drying 5% (v/v) aqueous microgel solutions some v/v % of added ethanol on Au coated substrates at, in part a 5%, in part b 10%, in part c 25%, in part d 50%, and in part e 75% (v/v) of ethanol. All of the photographs were taken after the microgel film was coated with a 2 nm Cr and 15 nm Au overlayer using a Pentax K-2000 DSLR camera. Bottom: DIC microscopy images for the corresponding films above, before Au coating with at in part a 5%, in part b 10%, in part c 25%, in part d 50%, and in part e 75% (v/v) of ethanol. Scale bars are 5 mm for the photographs, and 5 μm for the micrographs.

Figure 19:
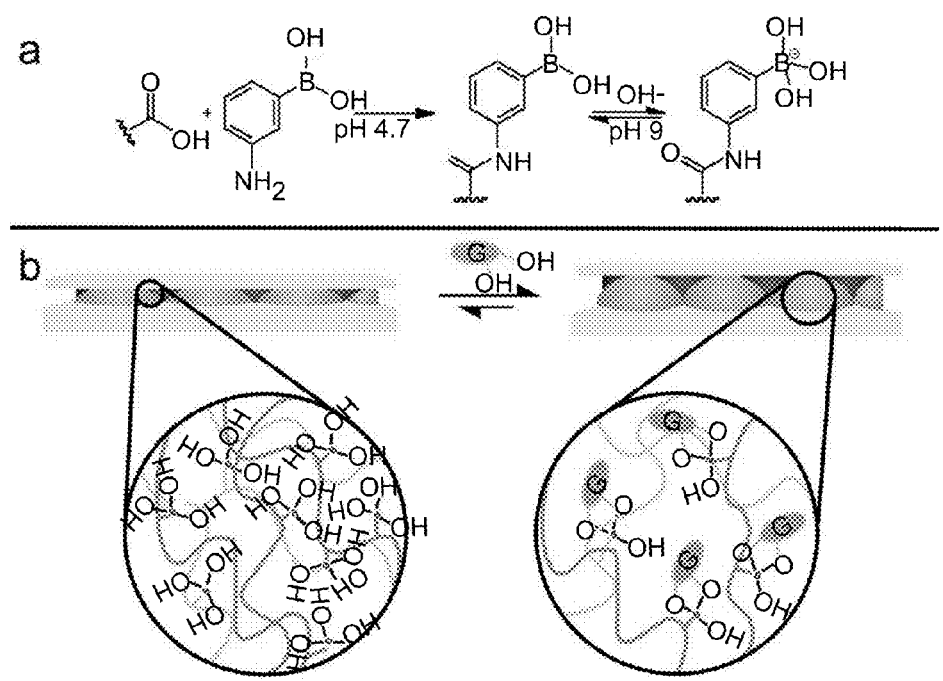

FIG. 19 shows (New 1 FIG. 1) Reaction scheme for, in part a, the functionalization of the acrylic acid moieties on the microgel with 3-aminophenylboronic acid (APBA) followed by the activation of the boronic acid with base, and in part b, a cartoon depiction of the glucose responsivity of an APBA-functionalized microgel etalon at pH 9.

Figure 20:
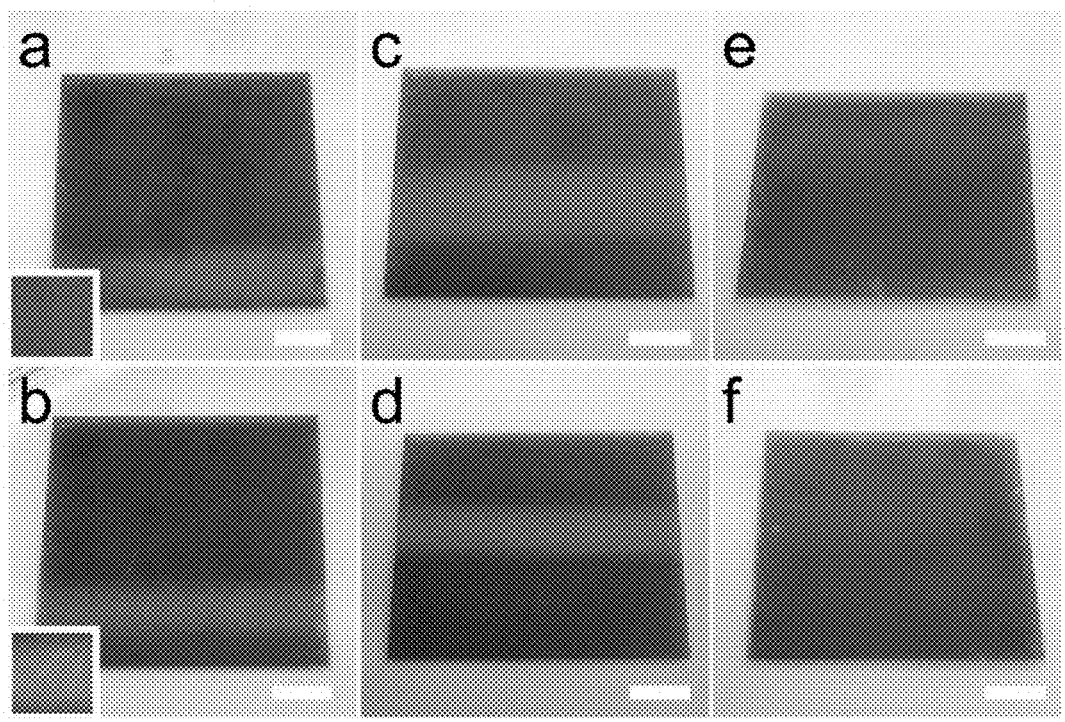

FIG. 20 shows (New 1 FIG. 5) APBA-functionalized microgel etalons are green, in part a, before glucose addition, but change to red, in part b, after glucose addition. The etalons fabricated by exposure to APBA only, show no significant change in color, in part c, before and, in part d, after glucose exposure. Similarly, the etalons exposed to EDC only, show no significant color change, in part e, before and in part f, after glucose exposure. Insets show a cropped image of the approximate center 1 cm² of each etalon. To make the etalon's color more apparent, the image brightness of the select region of the etalon was increased using image processing software. Scale bars are 5 mm.

DETAILED DESCRIPTION

In an embodiment, there is disclosed a gel assembly comprising a polymeric gel layer between metal layers. In another embodiment, there is disclosed a gel assembly process comprising providing a colloidal polymer in solution, drying the solution to form a polymeric gel layer and forming metal layers on either side of the polymeric gel layer. In a further embodiment, there is disclosed a method of drug delivery comprising loading a polymeric gel layer with drug, forming metal layers on either side of the polymeric gel layer, and wherein the polymeric gel layer comprises a material that is sensitive to a stimulus, and subjecting the polymeric gel layer to the stimulus to release the drug from between or through the metal layer or layers.

In various embodiments, one or more of the following features may be present in each of the four preceding embodiments:

The metal layers are reflective.

The metal layers are parallel to each other.

The metal layers are sufficiently thin to be transparent.

The metal layers have a different refractive index from the polymeric gel layer. In this instance, the gel assembly forms an etalon or interferometer. The thickness of the polymeric gel layer and the relative refractive indices of the layers determine the color of the etalon.

The polymer is a stimulus responsive material that changes volume in response to a stimulus. The stimulus may be for example temperature (thermoresponsive material), pH or ionic concentration (salt). The polymers may be responsive to more than one stimulus. Thus, for example a thermoresponsive polymer may also be hydroresponsive.

The stimulus responsive material comprises one or more of thermoresponsive polymers, pH responsive polymers, electroresponsive polymers, hydrophilic polymers, magnetoresponsive polymers, chemical responsive polymers, ionic strength responsive polymers and photoresponsive polymers;

By combining a stimulus responsive material with metal layers having a different refractive index from the polymeric gel layer, the gel assembly forms a tunable etalon or interferometer. When the wavelengths in which the gel assembly is operative are visible wavelengths then the gel assembly forms a color tunable etalon or interferometer.

The polymer is formed as a colloidal gel, and the polymeric gel layer is formed of particles that are closely packed or squeezed together to form a monolithic gel. The gel assembly should be monolithic, that is, as close to planar as possible. To achieve this with gel particles, the gel particles need to be jammed or squeezed together. This means the center to center particle distance is closer than what would be expected from the gel particle diameter alone. That is, with 1 micron diameter particles closely packed but not jammed together on a surface, the center to center distance would be 1 micron. A monolithic layer of microgels have center to center distances less than this, and are thus jammed together.

The nitrogen, fluorine, chlorine, or phosphorus in the monomer assists in binding the polymeric gel layer to the metal layers.

The polymeric gel layer may be a co-polymer formed of one or more co-monomers in addition to the monomer.

The monomer with the at least one nitrogen, fluorine, chlorine, or phosphorus per monomer unit may be the main monomer in a co-polymer.

The monomers in a co-polymer may be individually non-responsive to a stimulus or one or more of the co-monomers may be responsive to one or more stimuli. Different monomers in the co-polymer may be responsive to different stimuli.

The polymeric gel layer may be formed of colloidal particles having an effective diameter between 0.05 micron and 250 microns (a microgel falls within this size range), but smaller or larger particles are also expected to work. Tested materials include the range 0.229 micron to 1.5 microns but the process is not particularly sensitive to gel particle size and so may use a wider range of gel particle sizes.

The metal layers may be formed as coatings on the polymeric gel layer.

In the gel assembly process, the polymeric gel layer may be spread under pressure across a surface before being dried. Various tools may be used for spreading such as a roller, blade or brush. This process has particular utility for hydrogel particles (e.g., microgels).

Spreading occurs sufficiently rapidly and continuously to avoid different areas of the polymer drying at different times.

An example of a chemical responsive polymer is a glucose sensitive polymer.

The polymeric gel layer may be loaded with drug, for example for slow or controlled drug release.

In a gel assembly loaded for drug delivery, the polymeric gel may be spread onto a metal or other substrate. A solution containing drug is then added to the polymer layer and allowed to dry. A metal overlayer is then deposited on to the polymer and drug. The assembly is then exposed to a stimulus such as water in the case of a hydrosensitive polymer being used for the polymeric gel layer, and the drug released from the gel assembly. The release can also be triggered with temperature. That is, at high temperature, the gel particles in the gel assembly collapse, effectively squeezing out the drug on the polymer between the two metal layers. There may be other mechanisms of release for drug from a gel assembly loaded with drug. For example, polymer deswelling can cause cracks to form in the metal layer, which may facilitate more drug release at high temperature.

Any suitable method may be used to provide the metal layers on the polymeric gel layer. Such methods include, but are not limited to, physical vapor deposition, chemical vapor deposition, wet chemical methods, thermal evaporation, electron beam evaporation, sputtering, electrodeless deposition, pulsed laser deposition, and direct transfer of a metal layer from another substrate.

Time rate of swelling and deswelling of the gel assembly in the presence of a swelling or deswelling agent depends on metal layer thickness, and increases dramatically when the metal layer is very thin, for example less than 10 nm when the metal is gold and the deswelling or swelling agent is methanol. In other embodiments, the metal layers or at least one of the metal layers may be less than 20, 40, 60, 80 or 100 nm thick Any cross-linker suitable for the polymer forming the polymeric gel layer may be used for cross-linking monomers in the gel. Examples include N,N'-methylenebisacrylamide (effectively two acrylamide monomers joined at the N's by a methylene group). In some embodiments, the cross-linker may be omitted if the monomer units sufficiently bond to each other. For example, linear (uncrosslinked) poly(N-isopropylacrylamide) (pNIPAm) may be deposited by spin or dip coating pNIPAm on a metal such as Au, followed by Au or other metal deposition on top. Alternatively, NIPAm or other gel monomer can be spread on a Au or other metal surface and photopolymerized to make a polymeric gel layer, in this example a pNIPAm layer, onto which Au or other metal can be deposited. Photopolymerization allows the polymer layer to be patterned, however, other patterning methods may also be used. Patterning may be useful in, for example, display devices.

The polymer used for the polymeric gel layer may be any hydrogel or organogel (crosslinked polymer network that can be swollen with an organic solvent), but for it to be color tunable, the polymer must be responsive to a stimulus.

The gel assembly may be placed or formed on a flexible device, and individual spatially separated areas of the gel assembly may be used for sensing.

The gel assembly may be incorporated into a microbalance, such as a quartz crystal microbalance, for sensing using changes in resonant frequency of the microbalance.

Exemplary embodiments are disclosed in the following examples taken from the papers and their corresponding supplements published as: Paper A—Sorrell, C. D. et al., 2011, Color Tunable Poly (N-Isopropylacrylamide)-co-Acrylic Acid Microgel/Au Hybrid Assemblies, Adv. Funct. Mater. 21: 425-433

In this example, we disclose fabricating color tunable materials by exploiting the temperature and pH responsivity of pNIPAm-co-AAc microgels and their known ability to self-assemble on surfaces when dried. Specifically, when an aqueous solution of pNIPAm-co-AAc microgels is dried on Au coated glass substrates, the microgels have the tendency to dry into close packed arrays, producing robust, monolithic thin films of microgels. When coated with another layer of Au, these assemblies exhibit color, and in turn produce peaks in absorbance (reflectance) spectra, which are very sensitive to solution temperature and pH. We go on to characterize the structure of these materials, which reveals an etalon-like structure. These materials are novel with respect to responsivity, structure, sensitivity, and the nature by which they are assembled. By simply drying responsive microgels on a surface and subsequently coating with Cr/Au, a responsive, ordered structure (1D) can be fabricated without the need for more complex starting materials or assembly techniques. As mentioned above, the resulting structure reflects specific wavelengths of light, affording color, which is extremely sensitive to temperature and pH. This response is also highly reversible and the films are robust, and the film can be cycled from low to high temperature multiple times, at different pHs, while maintaining its color tunability and sensitivity.

Poly (N-isopropylacrylamide)-co-acrylic acid (pNIPAm-co-AAc) microgels crosslinked with 5% N,N'-methylenebisacrlyamide (BIS) and containing 10% AAc were synthesized (diameter ~1.3 µm in solution as determined by optical microscopy). The thermo- and pH-responsivity of pNIPAm-co-AAc microgels has been well documented. Briefly, pNIPAm-co-AAc microgels at pH 3.0 will collapse above ~31° C. and expel water, resulting in an increase in light scattering intensity. At pH 6.5, the microgel size is less affected by temperature, which is expected due to the Coulombic repulsion of the deprotonated AAc in the microgel, and the scattering intensity remains largely unchanged with increasing temperature. To confirm that our microgels behave as expected, scattering intensity of the synthesized microgels was measured as a function of pH and temperature and show the expected behavior.

A 5% solution of these microgels in deionized (DI) water (resultant solution pH ~4.72) was dried on a glass substrate coated with 2 nm of Cr followed by 15 nm of Au. In these studies, 2 nm of Cr is always used as an adhesion layer for Au and, for simplicity, will be omitted hereafter. The dried particle films are somewhat colored, as seen in the photograph in FIG. 1, part a (inset). Scanning electron microscopy (SEM) reveals a "monolithic" microgel film, as in FIG. 1, part a. This same experiment was repeated for a 5% microgel solution dried from phosphate buffered saline (0.02 M phosphate buffer with 150 mM sodium chloride, pH 7.2). While the films were also somewhat colored (FIG. 1, part b (inset)), the SEM in FIG. 1, part b, reveals a film with microgels spaced far apart from one another.

We coated each microgel film with 15 nm of Au (overlayer); the SEM images in FIG. 1, parts c and d, reveal that the overall morphology of the films remain unchanged. The deposition of the Au overlayer does not appear to damage the underlying microgel layer. In FIG. 1, part c, the Au layer can be seen completely coating the microgel layer deposited from water, essentially forming an independent, suspended layer on top of the microgels. The Au coated microgel films assembled from buffer resemble their structure before Au overlayer addition, as seen in FIG. 1, part d. Because of their sparse nature, the overlayer can be seen covering the particles and the underlying Au substrate. Despite the deposition conditions of the microgel layer the Au overlayer seems to be of high structural integrity and uniformity, as supported by secondary ion mass spectrometry (SIMS) imaging and SEM-Auger measurements.

Microgel films were also assembled from water on a bare glass surface. Au and microgel overlayers were added to this base microgel layer to make a multilayered assembly similar to those described above. The SEM image in FIG. 1, part e, shows that these films have the same monolithic structure as the films deposited from water onto Au substrates.

pNIPAm-co-AAc microgels in aqueous solution are both temperature and pH responsive, and as a result the assemblies should likewise be temperature and pH responsive. Therefore, we evaluated the spectral properties of these films while varying these external stimuli. Each film was mounted in a cuvette in a UV/Vis spectrometer by cutting the substrates down to ~1 cm$^2$ and taping them to the inside wall. At normal incidence, light readily passes through the films. Each film was immersed in either pH 3.0 or pH 6.5 solution and heated over a range of 25-40° C. while monitoring its absorbance (reflectance).

The spectra for the microgel films deposited from water at pH 3.0 show no temperature or pH dependent optical properties other than the increase in scattering intensity at low wavelength due to the temperature dependent microgel scattering, similar to what is observed in solution. The optical properties for this same film after addition of the Au are much different. These films show a main absorbance (reflectance) peak in the high wavelength region, which blue shifts with increasing temperature. We were also able to resolve a low wavelength peak, which similarly blue shifts with increasing temperature. We would like to point out that this optical behavior is not unique to a single film; we have fabricated many films by the same technique and have observed similar results. Similar spectral analysis of the film deposited from buffer doesn't reveal this type of optical behavior.

When the etalons fabricated from microgels in water are in pH 3.0 solution, the $\lambda_{max}$ for the high λ peak blue shifts ~300 nm over the 15° C. range, with the most dramatic shift occurring over 29-35° C. At pH 6.5, this behavior is suppressed and a much smaller blue shift is observed (~100 nm). We should point out here that we characterize the pH responsivity of our structures to prove that the microgels are still behaving as expected after being immobilized between the two Au layers. In a subsequent publication, the acid groups will be modified to render the microgel structure sensitive to various analytes for sensing purposes.

If the low λ peak is monitored a ~150 nm blue shift is observed over a 10° C. range before it becomes undetectable. Similar to the high λ peak, the low λ peak at pH 6.5 does not shift significantly with increasing temperature. We would also like to point out that at high temperature, a third peak becomes apparent at the high wavelength end of the spectrum. This behavior taken together is indicative of the different orders of reflection shifting as a result of the temperature induced film collapse, which brings the two Au layers closer to one another; a phenomenon observed for Fabry-Pérot etalons/interferometers. The thin film behavior also correlates very well with the behavior of the microgels in solution; the plots of $\lambda_{max}$ versus temperature closely resemble the LCST curve for the solution suspended microgels with a transition temperature of ~31° C.

The microgel films deposited from water onto bare glass show no color or color tunability. The behavior is very similar even after the addition of a Au overlayer to the original microgel film. Color tunability was only apparent after another microgel and Au layer was added on top of the base microgel/Au layers, such that two Au layers were now separated by a cavity made of microgels. The spectrum for this assembly shows the two-peak feature seen for the "etalons" fabricated from microgels in water. If the $\lambda_{max}$ for the high λ peak is plotted as a function of temperature a ~250 nm blue shift is observed over the 15° C. range at pH 3.0. As expected, the responsivity is suppressed at pH 6.5 and no significant wavelength shift is observed with increasing temperature.

We used two fabrication methods to determine if particle spacing yields a difference in optical properties. Particles deposited from water were closely packed, while films deposited from buffer displayed larger interparticle spacing, FIG. 1, parts a-d. We believe that the microgel films deposited from water are more closely packed than the films deposited from buffer because of their protonation state; microgels in water are less charged than they are in the high pH buffer which leads to less Coulombic repulsion between the particles allowing them to get closer to one another. Additionally, while the large spacing between the microgels deposited from buffer is likely due to Coulombic repulsion, it may also be due to buffer salt crystallizing on the surface during drying, effectively excluding microgels from the surface. Films made from microgels deposited from buffer do not exhibit color or color tunability when immersed in solution and heated, even though the Au overlayer can be seen covering the particles, FIG. 1, part d. This image also shows that the Au overlayer is pinned to the underlying Au substrate and clearly illustrates that an optical cavity is not formed (at least not on a large enough lateral length scale).

Since the microgel films are initially colored in the dry state, we hypothesized that: 1) the microgel films should remain somewhat colored when immersed in water, and 2) the color of the film should change as a function of temperature and/or pH. For this to be true, and for the color of the film to be reversible with temperature/pH changes, the Au/microgel bond should not be disrupted during the treatment. Photographs of the microgel films reveal that the films' integrity was not affected by solvation, temperature, or pH aside from a slight increase in color brightness after treatment (most notably for the film deposited from water). What is surprising is that the spectral color of the microgel films disappeared after immersing in pH 3.0 water, and the spectral properties did not change with temperature. Our initial hypothesis was based on the idea that the change in the refractive index of the microgels upon collapse would change the diffraction created by the particles and cause a spectral red shift. However, all we observe spectrally for these films is an increase in the scattering intensity of the films.

Figure 2:
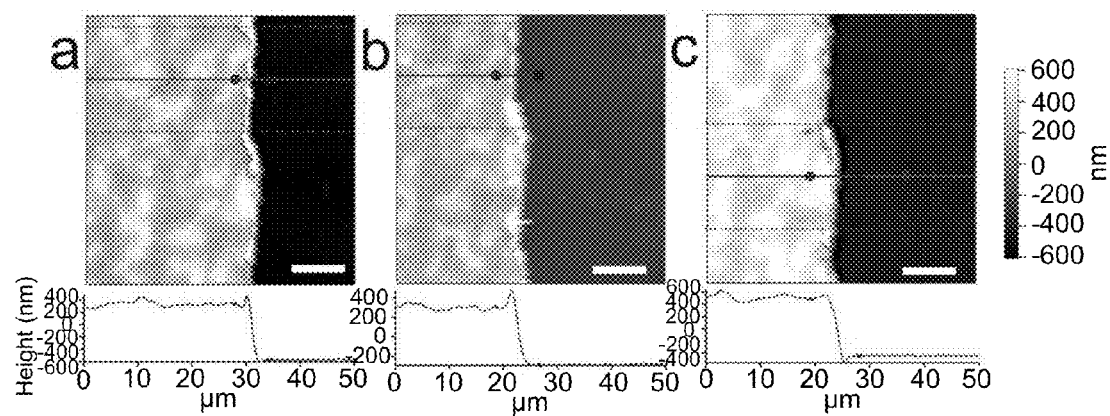

It is only after we deposit Au onto the microgel film deposited from water, that we observe optical properties in solution that are tunable with temperature and pH. The resultant assembly is similar structurally to an etalon; in our case, the etalon consists of a dielectric (microgels) sandwiched between two mirrors (Au). It is not immediately clear that one should be able to create a functional etalon from microgels because of the particulate nature of the resultant films. For an etalon to exist, the microgel film would need to be monolithic and not disassemble upon solvation. Further, the mirrors would need to be imperforated by the microgels themselves or by the overall swelling/ deswelling of the microgel film in response to temperature and pH. FIG. 2 shows AFM images for an etalon in pH 3.0 water as a function of temperature. A comparison of the film structure before and after heating suggests that the assembly remains intact and that the film morphology is largely unaffected by solvation and temperature variation; the RMS roughness for the film at low and high temperature is ~115 nm. These images support our hypothesis that we have fabricated a true, stable etalon structure. It is possible that the assemblies deposited from buffer create many individual etalon-like structures, but there is not enough of a collective response to exhibit color or color tunability.

These assemblies behave as etalons inasmuch as the light that passes through the Au overlayer is selectively reflected by the optical cavity. A typical spectrum produced by our etalons shows two peaks in the wavelength range we are monitoring (350-1000 nm). If the absorbance spectrum for a color tunable film is compared to its reflectance spectrum, the $\lambda_{max}$ for each is comparable, which indicates that the light that is being "adsorbed" by the film is actually being reflected. This is also true for a standard etalon and is described by elementary etalon theory.

Etalons exhibit multiple peaks at fixed wavelengths, which are related to the fringes formed by the interference of light passing through the cavity. Maxima of transmitted intensity occur where the light exiting the etalon interferes constructively, such that the following is satisfied:

$$2nd \cos \theta = p\lambda \qquad (1)$$

where $\lambda$ is the wavelength where the maxima occur, d is the mirror spacing, n is the refractive index of the material between the mirrors, $\theta$ is the angle of light in the film (related to the angle of incidence via Snell's Law) and p is an integer representing the order of the peaks. For a given n, d, and $\theta$, a maximum $\lambda$ will be observed in the spectrum at each p (i.e., p, p+1, p+2, . . . ). Our spectra give rise to two distinct peaks, and at some temperature points three peaks can be resolved. Currently, the peaks appear to be spaced apart by a constant $\lambda$, although we believe that the peaks are actually due to different orders of reflection.

The quality of the peaks arising from these assemblies can be described in terms of etalon finesse, which is a measure of the fringe quality and resolvability. An approximation of the finesse, F, can be determined from the following:

$$F \approx \frac{\Delta\lambda}{FWHM} \qquad (2)$$

where $\Delta\lambda$ is the separation of peaks, and FWHM is the full width at half maximum of a given peak. We estimate the finesse of our etalons to be ~2. Our average FWHM is ~115 nm, which is comparable to other colloidal photonic materials. Finesse can be affected by the appearance of large defects in the parallel mirrors. For our assemblies, the finesse does not change significantly as temperature or pH is modulated, so it is probable that the film is not becoming more heterogeneous, further supported by the AFM image analysis above. The finesse of these materials is most likely affected by the roughness necessarily present due to the particulate nature of the microgel layer between the Au layers, but can be affected by changing the reflectivity and nature of the mirrors. However, for this publication it is the change in the position of $\lambda_{max}$ in the absorbance spectrum as a function of pH and temperature that is of great value, and the observed finesse is high enough to easily resolve the peaks we wish to are monitor. By characterizing the sensitivity of $\lambda_{max}$ to temperature, we can determine the feasibility of these assemblies for sensing applications.

The soft, responsive microgels we use give us the ability to modulate the color of the assemblies (etalons) with minor changes of the etalon's environment, thus creating a tunable etalon, which is completely reversible. The observed blue shift in the spectra for microgel films deposited on bare glass from water after the addition of another microgel and Au layer, and deposited on Au from water after the addition of the Au overlayer with increasing temperature is equivalent to what would be observed for a standard etalon by bringing the two mirrors closer to one another. In our system, the distance between the two Au mirrors is modulated by the temperature dependent solvation state of the microgels, supported by the AFM images in FIG. 2. This is further confirmed by the fact that, at pH 6.5, minimal change in the position of the maxima as a function of temperature occurs, indicating that the spacing of the Au layers is relatively unchanged. The $\lambda_{max}$ versus temperature plots for the high $\lambda$ peaks, and low $\lambda$ peaks for etalons fabricated from microgels in water so closely resemble the microgels' behavior in solution that we can conclude that the microgels are not significantly altered by the deposition process or the presence of the Au overlayer.

Further evidence of the etalon structure comes from analysis of the particles dried on bare glass, which are subsequently covered with a Au overlayer. This structure does not afford any color or color tunability; it is only after a second microgel/gold bilayer is added to the base microgels/Au layers that the interesting tunable optical properties are observed. The wavelength shift for these assemblies built on glass is approximately the same in magnitude as our etalon material built on a Au substrate. The assemblies built on glass also exhibit the multiple absorption peaks typical of an etalon, and the expected pH dependent behavior. This further supports our hypothesis that the color tunability arises from the Au-Au spacing rather than from the particulate nature of the microgel film itself. We would also like to point out that as microgels collapse, their refractive index increases, which would result in a red shift according to eqation 1. While the refractive index of the microgel layer is necessarily increasing with increasing temperature, it is apparent that the modulation of the Au-Au mirror distance is controlling the optical properties of the materials.

Additionally, we are confident that the optical properties are not due to gold plasmon absorbance arising from nanosized Au regions on the microgel film surface. If this were a result of the Au film breaking up when immersed in liquid, or by the formation of Au islands due to gold dewetting, we would expect the absorbance to shift to higher wavelengths with increasing temperature due to film contraction. AFM analysis reveals that the assemblies are in fact contracting at high temperature; we directly observe a decrease of ~383 nm in the film's thickness as a result of an increase in temperature, FIG. 2 parts a and b. If there were Au nanoregions on the microgel thin film, they should get closer (aggregate) as a result of the film contraction at high temperature resulting in a red shift in the absorbance spectrum. We also point out that the film's roughness measured by AFM is very similar at low and high temperature, which further supports the fact that no surface defects are forming upon heating and that the Au film is homogenous independent of film solvation state. Their robustness indicates that these assemblies can be used in future studies to make multilayered optical materials.

Figure 3:
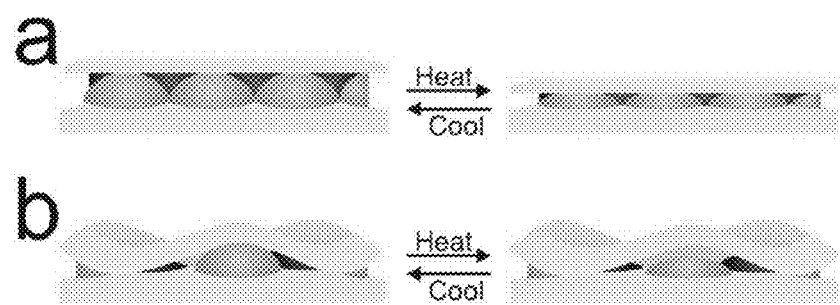
FIG. 3 shows (paper A Scheme 1) a cartoon depicting the proposed mechanism for the response of a microgel etalon fabricated in part a from water, and in part b from buffer. Response is shown as a function of temperature.

Taking into account all of the data, we propose a mechanism for the optical properties of the microgel etalons presented in this manuscript (FIG. 3). The microgels deposited from water essentially form a "monolithic" film and the Au overlayer is fully suspended by the microgel layer. This overlayer is held some distance away from the Au substrate, effectively forming a cavity. At pH 3.0, when the solution temperature is raised above the LCST of the microgels, and the microgels collapse, the Au layers approach one another uniformly, changing the interference properties of light, affecting the color of the etalon, as depicted in FIG. 3, part a. This is equivalent to changing the layer thickness between two mirrors in a traditional etalon, where the absorbance (reflectance) blue shifts as the two layers are brought closer to one another. Again, if this were a result of the particle refractive index changing, we would expect to see a red shift in the spectra.

The films deposited from buffer do not show color tunability because the spacing between the microgels is too large, and therefore the Au overlayer serves to coat both the microgels and the underlying Au layer. This effectively prevents the formation of a true etalon-like structure because the Au homogeneously coats both the microgel and the underlying Au layer and no cavity is formed, or at least not one large enough to give an optically measureable response. This structure also prevents the Au layers from uniformly approaching one another when heated, as depicted in FIG. 1, part b.

Finally, we modeled the optical behavior of these films assuming an etalon-like structure of two Au mirrors separated by a dielectric layer using Filmstar software (FTG Software Associates, Princeton, N.J.), which employs the matrix method and Maxwell's equations, as detailed by Macleod (H. A. Macleod, Thin-Film Optical Filters. 3rd ed.; Institute of Physics Publishing: London, 2001; p 641). We plugged in the nominal thicknesses for the Cr/Au layers and the thickness of the microgel layer determined by AFM, and used reported refractive index values for swollen and collapsed pNIPAm. The theoretically predicted optical properties agreed well with the experimentally observed values, that is, the shift in $\lambda_{max}$ with temperature predicted by theory very closely matches experiment. Any differences between the theoretical curves and experiment are most likely due to roughness of our films (which our model does not account for), and the lack of knowledge of the true value for the refractive index of the microgel layer. It is apparent from the modeling data, and the characterization presented herein, that the wavelength shift is due to the approach of the two Au mirrors as a result of the microgel thin film collapsing at high temperature.

We disclose a microgel etalon material with reversible color tunability in the visible region of the spectrum; peaks blue shift ~300 nm as the temperature of the solution is increased from 25-40° C. The materials are composed of temperature and pH responsive pNIPAm-co-AAc microgels, which are deposited on Au coated glass substrates from water or phosphate buffered saline pH 7.2 by a simple drying protocol. Films appear colored to the naked eye, but when their optical properties were evaluated in solution using a UV-vis spectrometer, there appears to be no selective reflection/transmission of certain wavelengths of light. Color tunability is only achieved after a Au overlayer is deposited on this microgel layer, and only for films made from the microgels deposited from water. Furthermore, the transition temperature of the films was approximately equal to that of the microgels in solution; at pH 3.0, the film and the microgels collapse at ~31° C. The analyses revealed that the structure of the optically responsive assembly is truly multilayered and that the Au overlayer was spatially separated from the Au substrate by a uniform microgel layer and is of high integrity. AFM imaging of the films deposited from water in solution revealed that the microgel layer thickness decreases by ~380 nm as a result of heating, bringing the Au layers closer to one another. The data suggest that it is the approach of the two Au layers that yields the observed optical properties. To further support this hypothesis, we conducted experiments on microgel particles deposited from water on bare glass with a Au overlayer. Color tunability is only exhibited after two Au layers have been deposited separated by a microgel layer.

N-isopropylacrylamide was purchased from TCI (Portland, Oreg.) and purified by recrystallization from hexanes (ACS reagent grade, EMD, Gibbstown, N.J.) prior to use. N,N'-methylenebisacrylamide (99%), acrylic acid (99%), and ammonium persufate (98+%) were obtained from Aldrich and were used as received. Various salts used for buffer solutions and for adjusting ionic strength were obtained from EMD and were used as received. All deionized water was 18.2 MΩ·cm obtained from a Milli-Q Plus system from Millipore (Billerica, Mass.). Au annealing was performed in an Isotemp muffle furnace from Fisher Scientific. Anhydrous ethanol was obtained from Commercial Alcohols (Brampton, Ontario). Hydrochloric acid was purchased from Caledon Chemicals (Alberta). Glass cover slips were 22×22 mm and obtained from Fisher Scientific. Cr and Au were 99.999% and obtained from ESPI (Ashland, Oreg.). Photographs of the films were taken with a Canon Powershot SD20 Digital ELPH SD.

Microgels composed of poly (N-isopropylacrylamide-co-acrylic acid) (pNIPAm-co-AAc) were synthesized via temperature-ramp, surfactant free, free radical precipitation polymerization as described previously. (Z. Meng, M. H. Smith, L. A. Lyon, 2009, Colloid Polym. Sci. 287: 277).

The monomer mixture was comprised of 85% N-isopropylacrylamide (NIPAm) and 10% acrylic acid (AAc) with 5% N,N'-methylenebisacrylamide (BIS) crosslinker (154 mM total monomer concentration). The monomer, NIPAm (8.5 mmol), and the crosslinker, BIS (0.51 mmol), were dissolved 50-mL deionized water (18.2 MΩ·cm) with stirring in a small beaker. The mixture was filtered through a 0.2 μm filter affixed to a 20 mL syringe into a 100 mL, 3-neck round bottom flask. An additional 12.5 mL of deionized water was used to wash the beaker, which was filtered and transferred to the round bottom flask. The flask was then fitted with a temperature probe, a condenser/$N_2$ outlet, stir bar, and a $N_2$ inlet. The monomer solution (62.5 mL total volume) was purged with $N_2$ gas for ~1 hr, with stirring at a rate of 450 rpm, while the temperature was allowed to reach 45° C. AAc (1.0 mmol) was added to the heated mixture with a micropipette. A 0.078 M aqueous solution of APS (2.5 mL) was delivered to the monomer solution with a transfer pipette to initiate the reaction. Immediately following initiation, a temperature ramp of 45° C. to 65° C. was applied to the solution at a rate of 30° C./hr. Following completion of the ramp, the reaction was allowed to proceed overnight at 65° C. After polymerization, the reaction mixture was filtered through glass wool to remove any large aggregates. The coagulum was rinsed with deionized water and the reaction solution was diluted to ~120 mL. A 12-mL aliquot of these particles was centrifuged at a speed of 8500 rcf at 20° C., to produce a pellet. The supernatant was removed from the pellet of particles, which were then resuspended to their original volume (12 mL) using deionized water. This process was completed a total of four times to remove unreacted monomer and linear polymer from the microgels.

Films were made from the cleaned particles by making a 10% dilution in either water or phosphate buffer. Since the original reaction solution was diluted ~2× from its initial concentration, a 10% solution is actually a 5% solution of microgels relative to the initial concentration. 600 µL of this solution was added to an ethanol rinsed and $N_2$ gas dried Cr/Au coated glass slide (22×22 mm) and covered, and allowed to dry overnight. Following drying, the slides were gently rinsed with DI water and dried with $N_2$ gas. The film's color tunability was evaluated, as detailed below, and then another Cr/Au layer was added as an overlayer. The films made on glass substrates were made in a similar fashion.

2 nm Cr and 15 nm of Au was added to an ethanol and $N_2$ gas dried glass coverslip at a rate of 1 Å $s^{-1}$, and 0.1 Å $s^{-1}$, respectively using a Torr International Inc. (New Windsor, N.Y.) thermal evaporation system Model THEUPG. The Cr/Au films were annealed at 250° C. for 3 h prior to microgel solution deposition.

Absorbance measurements were conducted on an Agilent 8453 UV-Vis, equipped with a 89090A temperature controller and Peltier heating device. Measurements were conducted by taping a film to the inside wall of a cuvette and adding either pH 3.0 or 6.5 solution (1 mM ionic strength adjusted with NaCl). The temperature was ramped between 25-40° C., and a spectrum was collected at every 1° C. after waiting 2.5 minutes at each temperature for stabilization. Spectra were collected over 190-1100 nm at an integration time of 0.5 s and an interval of 1 nm.

The thermoresponsivity of the microgels were studied at pH 3.0 and pH 6.5 using PTI fluorescence system (Birmingham, N.J., Model MP1, ser# 1621) and analyzed using FeliX32 Analysis Module (v1.2). To determine the scattering intensity of the microgels as a function of temperature, a solution of microgels (20.0 µL in 2.0 mL pH solution, either pH 3.0 or pH 6.5, 1 mM ionic strength) was irradiated at a wavelength of 600 nm and detected at a wavelength of 600 nm with slits open to ~0.62 mm. The temperature was ramped from 22-40° C. in 2° C. increments and the scattering intensity of the sample was measured for 300 s at each temperature (1 data point per second). The temperature was allowed to stabilize at each point for 300 s before the scattering intensity was monitored. The data for the scattering at each temperature was averaged for each 300 s measurement to determine the scattering intensity for each temperature, and the standard deviation was determined from the average.

Detailed images of the samples and microgels were taken with a LEO 1430 SEM. Samples in the SEM were tilted 85° (unless otherwise indicated) relative to the source. SEM contrast can be enhanced by addition of a metal layer on top of the microgel layer, however, since we were more interested in the long-range structure of the native microgel film, this is not done.

AFM images were acquired using an Asylum Research (Santa Barbara, Calif.) MFP 3D AFM equipped with a BioHeater closed fluid cell, which allowed the temperature of the imaging solution to be controlled using a feedback loop. Images were acquired over a 50×50 µm area, using a scan rate of 0.5 Hz, using 256 scan points and lines. The tips were Olympus TR800PSA with a frequency of 24 kHz. The images were collected on a scratched region of the film (scratched with a razor blade) in order to get an idea of the thickness of the film and how it changes with temperature. The AFM images were acquired in pH 3.0 solution at 25° C. and 40° C.

SIMS images were collected on ION-TOF SIMS IV (ION-TOF GmbH). A pulsed ion source (100 ps) at an interval of 100 µs was used. The substrate was scanned ~1000 times to generate the image. The beam size was ~300 nm. The image has a resolution of 128×128 line scans. The images were collected in static mode, using a current density of ~0.5 pA. Bi was used as an analytical source operated at 25 kV.

The SEM-Auger measurements were carried out using JAMP-9500F Auger microprobe (JEOL) at the Alberta Centre for Surface Engineering and Science, University of Alberta. The instrument is equipped with Shottky field emitter that produces electron probe diameter of about 3 to 8 nm at the sample. The accelerating voltage and emission current for both the SEM and Auger imaging were 10 kV and 8 nA, respectively. The working distance was 24 mm. The sample was rotated 30 degree away from the primary electron beam to face the electron energy analyzer. M5 lens with 0.6% energy resolution was used for the Auger spectroscopy and imaging. Etching was done using an Ar source. The emission current was 20 mA, the accelerating voltage was 2 kV. The etching area was 500×500 µm. Paper B—Sorrell, C.D., et al., 2011, Reflection order selectivity of color-tunable poly (N-isopropylacrylamide) microgel based etalons, Adv. Mater. 23; 4088-4092.

In this example, we disclose microgel etalons rationally designed to yield reflectance spectra with a specified number of reflectance peaks in the visible region of the electromagnetic spectrum. This is a significant extension of our previous work, where we report on the fabrication, characterization, and behavior of color tunable microgel based etalons. Here, we illustrate that desired optical properties can be predetermined, followed by the actual assembly of the desired material. This fact extends the utility of our materials by potentially enabling the technologies detailed above, which require a single reflectance peak in the visible region of the electromagnetic spectrum. To demonstrate this, a variety of microgels were synthesized of different diameters and softness. Specifically, three sets of microgels were synthesized with the same chemical composition, but different diameters; and two sets of microgels were synthesized with similar sizes, but different comonomer composition. Etalons were created from each set of microgels, and their optical properties were probed individually. While this is an extension of our previous work on microgel based etalons, it extend the utility of these materials.

The hydrodynamic diameter ($D_H$) values and the measured etalon thicknesses for all the microgels and assemblies in this study can be seen in Table 1. For all assemblies, the etalon thickness corresponds to —0.5-0.8 of the microgel diameter. As expected from equation 3:

$$\lambda m = 2nd \cos\theta \quad (3)$$

where λ is the wavelength maximum of the peak(s), m is the peak order, n is the refractive index of the dielectric, d is the spacing between the mirrors, and θ is the angle of incidence, the larger microgels yielded materials with many peaks in the visible region, while the smallest microgels yielded etalons with a single peak in the visible. A clear understanding of the relationship between microgel size, etalon thickness, and etalon spectral properties can provide a route to predicting the expected optical properties from a set of microgels with a $D_H$.

TABLE 1

Physical properties of microgels and their resultant etalons.

| Microgel | Hydro-dynamic diameter, $D_H$ [nm] [a] | Etalon thickness [nm] [b] | # of Spectral Peaks | Average Experimental $\lambda_{max}$ for each peak [nm] [c] | Experimental Order [d] | Theoretical Order | Theoretical $\lambda_{max}$ for each peak [nm] [e] | Theoretical Free Spectral Range (FSR), $\Delta\lambda$ [nm] [f] |
|---|---|---|---|---|---|---|---|---|
| pNIPAm-co-AAc-1 | 1548 (±69) | 1004 (±98) | 5 | 853 (±13) | 3.23 | 3 | 917 | 284 |
|  |  |  |  | 693 (±10) | 3.97 | 4 | 688 | 173 |
|  |  |  |  | 588 (±7) | 4.68 | 5 | 550 | 118 |
|  |  |  |  | 511 (±5) | 5.38 | 6 | 458 | 85 |
|  |  |  |  | 452 (±6) | 6.09 | 7 | 393 | 65 |
| pNIPAm-co-AAc-2 | 659 (±21) | 440 (±36) | 3 | 713 (±47) | 1.69 | 2 | 603 | 357 |
|  |  |  |  | 510 (±34) | 2.36 | 3 | 402 | 170 |
|  |  |  |  | 400 (±32) | 3.01 | 4 | 301 | 100 |
| pNIPAm-co-AAc-3 | 229 (±10) | 127 (±16) | 1 | 535 (±24) | 0.65 | 1 | 348 | ~ |
| pNIPAm-co-AAm | 653 (±10) | 544 (±56) | 4 | 829 (±7) | 1.80 | 2 | 745 | 415 |
|  |  |  |  | 591 (±8) | 2.52 | 3 | 497 | 197 |
|  |  |  |  | 460 (±14) | 3.24 | 4 | 373 | 115 |
|  |  |  |  | 374 (±9) | 3.99 | 5 | 298 | 75 |
| pNIPAm-co-VAA | 603 (±17) | 347 (±46) | 2 | 658 (±26) | 1.44 | 2 | 475 | 329 |
|  |  |  |  | 468 (±22) | 2.03 | 3 | 317 | 156 |

[a] Determined by PCS (±standard deviation of 5 measurements).
[b] Determined by AFM imaging (±standard deviation of height over 100 line scan averages on three areas each for three images).
[c] Averaged from the $\lambda_{max}$ for each peak from at total of 6 spectra at different areas on two different etalons (±standard deviation).
[d] Calculated using equation 4, where n = 1.37 and θ = 0.
[e] Calculated using equation 3, where m is the theoretical order.
[f] Calculated using equation 5, where m is the theoretical order and $\lambda_0$ is the average experimental $\lambda_{max}$ for each peak. FSR was not calculated for pNIPAm-co-AAc-3 etalon since there is only one experimental spectral peak where m = 1 indicating there is no theoretical adjacent peak.

FIG. 9 shows the spectra for each etalon, along with photographs of the dry and hydrated assemblies. By inspection, it is apparent that each spectrum is distinct with respect to the number and position of the reflectance peaks. Furthermore, the photographs show that each etalon exhibits a characteristic color and brightness in both their dry and hydrated state. The thickest etalon (FIG. 9, part a) was fabricated using pNIPAm-co-AAc microgels with a nominal $D_H$ of ~1.5 µm (hereafter referred to as pNIPAm-co-AAc-1). The etalon's spectrum has 5 distinct peaks in the visible region of the electromagnetic spectrum. Another etalon was assembled from pNIPAm-co-AAc microgels with a $D_H$ of ~660 nm (pNIPAm-co-AAc-2), therefore equation 3 predicts that there should be fewer peaks in this visible, for the same dielectric refractive index. As can be seen in FIG. 9, part c, this etalon only exhibits 3 reflectance peaks in the spectrum. Furthermore, another etalon was fabricated using pNIPAm-co-AAc microgels with a nominal $D_H$ of ~230 nm (pNIPAm-co-AAc-3). This etalon's spectrum has only 1 distinct peak at ~535 nm, FIG. 9, part e.

Two additional etalons were constructed from pNIPAm microgels synthesized with two different comonomers; one set of microgels contained acrylamide, while the other contained vinylacetic acid. The pNIPAm-co-acrylamide (pNIPAm-co-AAm) and pNIPAm-co-vinylacetic acid (pNIPAm-co-VAA) microgels both exhibited $D_H$ values comparable to the pNIPAm-co-AAc-2 microgels. It is clear from the data in Table 1, however, that while they have comparable $D_H$, they each result in etalons with different dielectric thicknesses (d). Since each of these three microgels have similar $D_H$ the different resulting thicknesses must be a result of differences in microgel softness, which result in thicker/thinner films accordingly. Therefore, the microgels produce distinct spectra due to their differences in d. Of these three, the pNIPAm-co-AAm microgel etalon has the highest dielectric thickness; as a result, its spectrum exhibits four reflectance peaks. The spectrum for the etalon constructed from pNIPAm-co-vinylacetic acid (pNIPAm-co-VAA) microgels exhibits only two resolvable peaks in the range 350-1000 nm, and is about half the thickness of the pNIPAm-co-AAm microgel etalon. The pNIPAm-co-AAc-2 etalon has a dielectric thickness between the pNIPAm-co-AAm and pNIPAm-co-VAA etalons, and exhibits an intermediate number of peaks in its reflectance spectrum. Therefore, we conclude that that dielectric thickness really is the most important parameter we can modify to design etalons with desired spectral properties.

A simple analysis of the etalons' spectra can be performed by solving equation 3 for m and calculating the order for each observed λ, using the thickness measured using atomic force microscopy (AFM) for d, and 1.37 for n.

$$m = \frac{2nd\cos\theta}{\lambda} \qquad (4)$$

The results of this analysis are shown in Table 1. Each etalon exhibits peaks in their spectra that increase in order with decreasing wavelength, although the calculated orders are not whole numbers. Nonetheless, we assigned whole number orders to each peak in the observed spectra in FIG. 9, parts a-e, as shown in Table 1.

Using the assigned order values, the theoretical $\lambda_{max}$ values were calculated for each etalon using equation 3 and are reported in Table 1. These data show that for most of the etalons one or more of the experimentally observed peaks very closely match the calculated values. For simplicity, we can number the peaks $\lambda_1$ through $\lambda_5$ starting with the most red-shifted for the pNIPAm-co-AAc-1 etalon where $\lambda_1$=853. The data in Table 1 show that the experimentally observed $\lambda_2$, $\lambda_3$, and $\lambda_5$ peaks at 693 nm, 588 nm, and 452 nm, respectively, very closely correspond to the theoretical $\lambda_{max}$ where the theoretical m=4, 5, and 6. The remaining peaks in the spectrum are similar to the calculated expected values, but do not correspond as closely indicating that there may be other factors contributing to abnormalities in the spectra.

Using the measurements in Table 1, we can verify our peak order assignments by calculating free spectral range (FSR, or $\Delta\lambda$) using the equation:

$$\Delta\lambda = \frac{\lambda_0^2}{2nd\cos\theta} \quad (5)$$

where $\lambda_0$ is the wavelength under investigation, and $\Delta\lambda$ is the distance to its adjacent peak. We can substitute the inverse of equation 4 into equation 5 and simplify the expression to:

$$\Delta\lambda = \lambda_0 \frac{1}{m} \quad (6)$$

where m is the integer value assigned for the peak order. To compare the analysis of FSR to the analysis of order and theoretical peak values, we look again at the spectrum for the pNIPAm-co-AAc-1 etalon and use the same peak numbering scheme described above. In this analysis we start by calculating FSR for the peak at the average wavelength value of $\lambda_5$ at 452 nm. The FSR will provide for us the $\Delta\lambda$ between $\lambda_5$ and its adjacent peak, $\lambda_4$. Using equation 5 and the experimentally obtained etalon properties in Table 1 (for $\lambda$, n and d) we obtain a FSR of 74 nm; alternately, using equation 4 and m=7 as assigned for $\lambda_5$ (Table 1), we obtain a FSR of 65 nm.

The experimental $\Delta\lambda$ between $\lambda_5$ and $\lambda_4$ is ~59 nm, indicating that the experimentally obtained values for the etalon's physical properties are precise enough to allow us to calculate m using equation 4 for each peak, and that our assigned theoretical m integer values are accurate. We can therefore continue the series by calculating the FSR (using equation 6) and obtain calculated $\Delta\lambda$ values that closely correspond to the experimentally obtained peak distances for each of the experimentally obtained spectra (Table 1). We hypothesize that any discrepancies between experimental spectra and theory result from our devices being inherently imperfect due to the nature of the microgel based dielectric layer, while the equations used were developed for ideal systems that assume perfect planar mirrors, isotropic dielectric refractive index, and the use of a collimated and polarized light source. This hypothesis is supported by a simple analysis of the shape and appearance of the reflectance peaks. For example, many of our etalons exhibit features such as non-Gaussian peak shapes ($\lambda_1$ in FIGS. 9, parts b and c) and peak shoulders (FIG. 9, part e). We may be able to alleviate these issues by using a collimated or polarized light source, but any inhomogeneities imparted by the particulate structure of the dielectric will remain. Our system, while functional, does not strictly adhere to the properties required to apply equation 3. However, the fact we can calculate any meaningful data at all is a testament to their novelty and future utility. In summary, we can control the number and order of reflection peaks a pNIPAm microgel based etalon exhibits in the visible region of the electromagnetic spectrum by changing the size and mechanical properties of the microgels. Using microgels with radically different hydrodynamic diameter to vary the dielectric thickness (d) allows us to design and construct etalons that exhibit spectra with multiple or a single reflectance peaks, as well as a distinct visual color. Furthermore, microgels of a similar size and different mechanical properties, where softer microgels yield an etalon with a smaller dielectric thickness compared to stiffer microgels, will also create etalons with distinctive spectral properties and color. Our analysis of the resolution of the etalon spectra using FSR calculations indicates that our materials adhere very closely to our calculations and assignments of peak order, m. This work has led toward a greater understanding of what dictates microgel etalon color and spectral behavior. It is a first step towards directed materials fabrication and the development of etalons that display a single visible color.

N-isopropylacrylamide was purchased from TCI (Portland, Oreg.) and purified by recrystallization from hexanes (ACS reagent grade, EMD, Gibbstown, N.J.) prior to use. N,N'-methylenebisacrylamide (BIS) (99%), acrylic acid (AAc) (99%), 3-butenoic acid (vinylacetic acid, VAA) (97%), acrylamide (AAm) (≥99%), formic acid (50% in water), and ammonium persulfate (APS) (98+%) were obtained from Sigma-Aldrich (Oakville, Ontario) and were used as received. Sodium chloride and sodium hydroxide were obtained from Fisher (Ottawa, Ontario). All deionized water was filtered to have a resistivity of 18.2 MΩ·cm and was obtained from a Milli-Q Plus system from Millipore (Billerica, Mass.). Au annealing was performed in a Thermolyne muffle furnace from Thermo Fisher Scientific (Ottawa, Ontario) Anhydrous ethanol was obtained from Commercial Alcohols (Brampton, Ontario). Glass cover slips were 25×25 mm and obtained from Fisher Scientific (Ottawa, Ontario). Cr and Au were 99.999% and obtained from ESPI (Ashland, Oreg.). Photographs of the films were taken with a Pentax K2000 DSLR camera fitted with a SMC Pentax-DA 1:2.8 35-mm rectilinear macro lens.

pNIPAm-co-AAc-1. The microgels were synthesized following a previously published procedure (Z. Meng, M. H. Smith, L. A. Lyon, 2009, Colloid Polym. Sci. 287: 277). N-Isopropylacrylamide (NIPAm, 17.0 mmol) and N,N'-methylenebisacrylamide (BIS, 1.00 mmol) were added to 100 mL of deionized water in a small beaker and stirred. Once dissolved, the solution was filtered through a 0.2 μm filter in a 3-neck flask. The beaker was rinsed with 25 mL of deionized water and the rinsate was filtered into the flask. The flask was fitted with a condenser, a nitrogen inlet, and a temperature probe to provide heating via a feedback-loop controlled hotplate (Torrey Pines Scientific, Carlsbad, Calif.). The flask was heated in an oil bath to 45° C. while the solution was allowed to stir and purge with $N_2$ over about 1.5 hours. Then acrylic acid (AAc, 2.00 mmol) was added in one aliquot. The reaction was then initiated with a 0.078 M aqueous solution of ammonium persulfate (APS, 5 mL). After initiation, the reaction solution was then heated at a rate of 30° C./hour to 65° C. and the reaction was allowed to proceed overnight under a blanket of nitrogen. The resulting suspension was allowed to cool to room temperature, and then it was filtered through a plug of glass wool to remove any coagulum formed during the reaction. The microgel solution was then distributed into centrifuge tubes and purified via centrifugation at ~8300 rcf to form a pellet, followed by removal of the supernatant and resuspension with deionized water, 6×. The cleaned microgels were recombined and stored in a brown glass jar.

pNIPAm-co-AAc-2. The microgels were synthesized following a previously published procedure (M. J. Serpe, C. D. Jones, L. A. Lyon, 2003, Langmuir 19: 8759). A 3-neck flask was fitted with a reflux condenser, nitrogen inlet, and temperature probe (as above), and charged with a solution of NIPAm (11.9 mmol) and BIS (0.703 mmol) in 99 mL deionized water, previously filtered through a 0.2 μm filter. The solution was purged with $N_2$ and allowed to heat to 70° C. over ~1 hour. AAc (1.43 mmol) was added to the heated reaction mixture in one aliquot. The reaction was then initiated with a solution of APS (0.2 mmol) in 1 mL of deionized water. The reaction was and allowed to proceed at 70° C. for 4 hours under a blanket of nitrogen. The resulting suspension was allowed to cool overnight, and then it was filtered through a Whatman #1 paper filter to remove any large aggregates. The microgel solution was then distributed into centrifuge tubes and purified via centrifugation at ~8300 rcf to form a pellet, followed by removal of the supernatant and resuspension with deionized water, 6×. The cleaned microgels were recombined and stored in a brown glass jar.

pNIPAm-co-AAc-3. The microgels were synthesized following a previously published procedure (C. D. Jones, L. A. Lyon, 2000, Macromolecules 33: 8301). A 3-neck flask was fitted with a reflux condenser, nitrogen inlet, and temperature probe (as above), and charged with a solution of NIPAm (11.1 mmol), BIS (0.652 mmol), and sodium dodecyl sulfate (SDS, 0.2 mmol) in 190 mL deionized water, previously filtered through a 0.2 μm filter. The solution was purged with $N_2$ and allowed to heat to 70° C. over ~1 hour. AAc (1.30 mmol) was added to the heated reaction mixture in one aliquot. The reaction was then initiated with a solution of APS (0.3 mmol) in 10 mL of deionized water. The reaction was and allowed to proceed at 70° C. for 4 hours under a blanket of nitrogen. The resulting suspension was allowed to cool overnight, and then it was filtered through a Whatman #1 paper filter to remove any large aggregates. Approximately half of the microgel solution was then distributed into rehydrated dialysis tubing (12-14k nominal MWCO, 25 mm flat width, Fisherbrand Regenerated Cellulose, Nepan, ON) for purification. The tubes were placed into two 2 L beakers with deionized water and a stir bar for two weeks and the water was replaced 2× daily. The cleaned microgels were recombined and stored in a brown glass jar.

pNIPAm-co-AAm. The microgels were synthesized in the same manner as the pNIPAm-co-AAc-2 microgels. A 3-neck flask was fitted with a reflux condenser, nitrogen inlet, and temperature probe (as above), and charged with a solution of NIPAm (11.9 mmol), BIS (0.704 mmol), and AAm (1.40 mmol) in 99 mL deionized water, previously filtered through a 0.2 μm filter. The solution was purged with $N_2$ and allowed to heat to 70° C. over ~1 hour. The reaction was then initiated with a solution of APS (0.2 mmol) in 1 mL of deionized water. The reaction was and allowed to proceed at 70° C. for 4 hours under a blanket of nitrogen. The resulting suspension was allowed to cool overnight, and then it was filtered through a Whatman #1 paper filter to remove any large aggregates. The microgel solution was then distributed into centrifuge tubes and purified via centrifugation at ~8300 rcf to form a pellet, followed by removal of the supernatant and resuspension with deionized water, 6×. The cleaned microgels were recombined and stored in a brown glass jar.

pNIPAm-co-VAA. The microgels were synthesized in the same manner as the pNIPAm-co-AAc-2 microgels. A 3-neck flask was fitted with a reflux condenser, nitrogen inlet, and temperature probe (as above), and charged with a solution of NIPAm (11.9 mmol) and BIS (0.695 mmol) in 99 mL deionized water, previously filtered through a 0.2 μm filter. The solution was purged with $N_2$ and allowed to heat to 70° C. over ~1 hour. VAA (1.40 mmol) was added to the heated reaction mixture in one aliquot. The reaction was then initiated with a solution of APS (0.2 mmol) in 1 mL of deionized water. The reaction was and allowed to proceed at 70° C. for 4 hours under a blanket of nitrogen. The resulting suspension was allowed to cool overnight, and then it was filtered through a Whatman #1 paper filter to remove any large aggregates. The microgel solution was then distributed into centrifuge tubes and purified via centrifugation at ~8300 rcf to form a pellet, followed by removal of the supernatant and resuspension with deionized water, 6×. The cleaned microgels were recombined and stored in a brown glass jar.

Etalons were fabricated following a previously published procedure (C. D. Sorrell, M. C. D. Carter, M. J. Serpe, 2011, ACS Appl. Mater. Interfaces, 3: 1140). To fabricate the Au coated coverslips (etalon underlayer), 2 nm Cr and 15 nm of Au was added to a 25×25 mm ethanol rinsed and $N_2$ gas dried glass coverslip (Fisher's Finest, Ottawa, ON) at a rate of 1 Å $s^{-1}$, and 0.1 Å $s^{-1}$, respectively (Torr International Inc., thermal evaporation system, Model THEUPG, New Windsor, N.Y.). The Cr/Au substrates were annealed at 250° C. for 3 h (Thermolyne muffle furnace, Ottawa, ON) and cooled to room temperature prior to microgel film deposition.

Approximately 5-10 mL of microgel solution was centrifuged at ~8300 rcf to form a pellet. The supernatant was removed and discarded, and the pellet was vortexed to loosen and homogenize the particles in the remaining solvent. A 40 uL aliquot of concentrated microgels were spread onto an annealed 25 mm×25 mm Au-coated glass coverslip. The film was allowed to dry on a 30° C. hotplate for 30 minutes before the excess microgels were rinsed with deionized water. The samples were soaked overnight at 30° C. in a deionized water bath. The samples were then rinsed with deionized water, dried with $N_2$, and another Au overlayer (2 nm Cr for adhesion, followed by 15 nm Au) was added. The completed device was soaked overnight in deionized water at 30° C. before spectral analysis.

Reflectance measurements were conducted using a Red Tide USB650 spectrometer, a LS-1 tungsten light source, and a reflectance probe from Ocean Optics (Dunedin, Fla.). The spectra were recorded using Ocean Optics Spectra Suite Spectroscopy Software at room temperature over a wavelength range of 400-1000 nm. Measurements were conducted by placing the film in temperature-controlled chamber with 10 mM formic acid buffer (pH 3, 10 mM ionic strength due to NaCl) at 25° C. The probe height was adjusted above the film for optimal signal. The probe remained undisturbed between measurements to ensure that all of the spectra were taken in the same manner. The film was moved using an XY stage under the probe and three measurements were taken for each film. We determined at the thermoresponsivity of the films by measuring spectra every 2° C. over a temperature range of 23-39° C.

PCS measurements were performed using a Brookhaven Instruments ZetaPlus zeta potential analyzer and ZetaPlus microgel sizing software v.5 (Holtsville, N.Y.). All measurements were taken at 25° C. in 10 mM formate buffer (pH 3, 10 mM ionic strength due to NaCl). Each hydrodynamic diameter is reported as an average of five 30 s acquisitions and averaged over five measurements per sample.

Images were acquired using an Asylum Research (Santa Barbara, Calif.) MFP 3D AFM. Each image was acquired over a 50 μm×50 μm area, using a scan rate of 0.3 Hz, using 512 scan points and lines. The tips were Olympus TR800PSA with a frequency of 24 kHz. The films were hydrated via sessile drop using 10 mM formate buffer (pH 3, 10 mM ionic strength due to NaCl). The images were collected on a scratched region of an etalon (scratched with a razor blade) in order to get an idea of the thickness of the solvated film. A total of 34 nm was subtracted from each thickness to correct for the thickness of the mirrors. Paper C—Sorrell, C. D., et al., 2011, A "Paint-On" Protocol for the Facile Assembly of Uniform Microgel Coatings for Color Tunable Etalon Fabrication, ACS Appl. Mater. Interf. 3: 1140-1147

In this example, we disclose microgels with a variety of chemical functionalities painted on Au coated substrates to yield dense polymer coatings, further expanding the utility of the method. It appears that microgel functionality does not affect the quality of the resulting film. The coatings also appear to be extremely robust, and we demonstrate that the technique can be applied to Au coated glass, plastic, and clean Si substrates.

N-isopropylacrylamide was purchased from TCI (Portland, Oreg.) and purified by recrystallization from hexanes (ACS reagent grade, EMD, Gibbstown, N.J.) prior to use. N,N'-methylenebisacrylamide (BIS) (99%), acrylic acid (AAc) (99%), 3-butenoic acid (vinylacetic acid, VAA) (97%), acrylamide (AAm) (≥99%), formic acid (50% in water), and ammonium persulfate (APS) (98+%) were obtained from Sigma-Aldrich (Oakville, Ontario) and were used as received. Various salts used for buffer solutions and for adjusting ionic strength were obtained from EMD and were used as received. All deionized (DI) water was filtered to have a resistivity of 18.2 MΩ·cm and was obtained from a Milli-Q Plus system from Millipore (Billerica, Mass.). Au annealing was performed in a Thermolyne muffle furnace from Thermo Fisher Scientific (Ottawa, Ontario) Anhydrous ethanol was obtained from Commercial Alcohols (Brampton, Ontario). Hydrochloric acid was purchased from Caledon Chemicals (Georgetown, Ontario). Fisher's Finest glass cover slips were 25×25 mm and obtained from Fisher Scientific (Ottawa, Ontario). Transparencies were from Canon Inc. (Lake Success, N.Y.). Silicon wafers (1-0-0, N-type, 0.5 mm thick) were obtained from University Wafer (Boston, Mass.). Cr and Au were 99.999% and obtained from ESPI (Ashland, Oreg.). Photographs of the films were taken with an Olympus C-7070 Wide Zoom or a Pentax K2000 DSLR camera fitted with a SMC Pentax-DA 1:2.8 35-mm rectilinear macro lens.

Microgels composed of poly (N-isopropylacrylamide-co-acrylic acid) (pNIPAm-co-AAc-1) were synthesized via temperature-ramp, surfactant free, free radical precipitation polymerization following a previously published procedure (Meng, Z.; Smith, M. H.; Lyon, L. A., 2009, Colloid Polym. Sci., 287: 277). The monomer mixture was comprised of 85% N-isopropylacrylamide (NIPAm) and 10% acrylic acid (AAc) with 5% N,N'-methylenebisacrylamide (BIS) crosslinker (154 mM total monomer concentration). The monomer, NIPAm (8.5 mmol), and the crosslinker, BIS (0.51 mmol), were dissolved in deionized water (50 mL) with stirring in a small beaker. The mixture was filtered through a 0.2 μm filter affixed to a 20 mL syringe into a 100 mL, 3-neck round bottom flask. An additional aliquot of deionized water (12.5 mL) was used to wash the beaker, which was filtered and transferred to the round bottom flask. The flask was then fitted with a temperature probe, a condenser/$N_2$ outlet, stir bar, and a $N_2$ inlet. The monomer solution (62.5 mL total volume) was purged with $N_2$ gas for ~1 hr, with stirring at a rate of 450 rpm, while the temperature was allowed to reach 45° C. AAc (1.0 mmol) was added to the heated mixture with a micropipette. A 0.078 M aqueous solution of APS (2.5 mL) was delivered to the monomer solution with a transfer pipette to initiate the reaction (total reaction volume 65.0 mL). Immediately following initiation, a temperature ramp of 45° C. to 65° C. was applied to the solution at a rate of 30° C./hr. Following completion of the ramp, the reaction was allowed to proceed overnight at 65° C. After polymerization, the reaction mixture was filtered through glass wool to remove any large aggregates. The coagulum was rinsed with deionized water and the reaction solution was diluted to ~120 mL (diluted approximately 2× from the original microgel solution concentration). An aliquot of these microgels (12 mL) was centrifuged at a speed of ~8400 relative centrifugal force (rcf) at 23° C., to produce a pellet at the bottom of the centrifuge tube. The supernatant was removed from the pellet of microgels, which were then resuspended to their original volume (12 mL) using deionized water. This process was completed a total of four times to remove unreacted monomer and linear polymer from the microgels.

Microgels were also synthesized using other previously described techniques (Serpe, M. J.; Jones, C. D.; Lyon, L. A., 2003, Langmuir, 19: 8759; Jones, C. D.; Lyon, L. A., 2000, Macromolecules, 33: 8301) without a co-monomer (pNIPAm-BIS microgels, 5% crosslinker), as well as with vinylacetic acid (pNIPAm-co-VAA, 10 mol %) and acrylamide (pNIPAm-co-AAm, 10 mol %) comonomers. Medium (pNIPAm-co-AAc-2) and small (pNIPAm-co-AAc-3) diameter acrylic acid (10 mol %) microgels were also synthesized. Crosslinker concentration for all syntheses was 5 mol % and the NIPAm amount was adjusted accordingly to accommodate the respective comonomer.

To fabricate the Au coated coverslips (etalon underlayer), 2 nm Cr and 15 nm of Au was added to a 25×25 mm ethanol rinsed and $N_2$ gas dried glass coverslip at a rate of 1 Å s$^{-1}$, and 0.1 Å s$^{-1}$, respectively, using a Torr International Inc. (New Windsor, N.Y.) thermal evaporation system Model THEUPG. The Cr/Au films were annealed at 250° C. for 3 h and cooled to room temperature prior to microgel solution deposition.

Transparency slides were cut to an approximate dimension of 25 mm×80 mm, rinsed with ethanol and dried with $N_2$. The cut pieces were affixed to a microscope slide with tape, and 2 nm Cr and 15 nm of Au were evaporated onto the substrate as above.

Silicon wafers were cut to an approximate dimension of 25 mm×25 mm and cleaned with piranha solution (75:25 $H_2SO_4$:$H_2O_2$) for 30 minutes. The cleaned substrates were rinsed copiously with water and dried with $N_2$ prior to Au coating.

"Paint-on" technique. For most syntheses, an aliquot of a given microgel solution (above) was centrifuged for 30 minutes at 23° C. at ~8400 relative centrifugal force (rcf) in order to pack the microgels into a concentrated pellet. Microgels with a small diameter were centrifuged at 29° C. for 2 hours at ~8400 rcf. The supernatant was removed. An annealed 25×25 mm Au coated glass substrate was rinsed with EtOH and dried with $N_2$ and was placed onto hot plate set to 30° C. along with the tube containing the microgel pellet, for about 5 minutes. A 40 μL aliquot of the concentrated microgels was deposited onto the Au substrate, and spread toward each edge using the side of a micropipette tip, taking care not to scratch the Au substrate. The film was rotated 90° and the microgel solution was spread again. The spreading and rotation continued as the microgel layer dried. To avoid having the microgels stick to the tip of the pipette—compromising the microgel film quality—the spreading ceased when the layer became noticeably viscous. The microgels were allowed to dry completely by increasing the hot plate temperature to 35° C. and allowing the film to dry at that temperature for 2 h. The film was rinsed copiously with deionized water to remove any excess microgels. The film was then placed into a deionized water bath and allowed to sit overnight at ~30° C.

The same protocol was used for the silicon substrates. It was also used to coat the Au coated transparency slide, with the exception that the quantity of concentrated microgels was increased to 80 µl to cover the larger substrate, which was not annealed prior to coating.

Films were made from the cleaned microgels using the above "paint-on" method. Following film drying and overnight soaking, the slides were rinsed with DI water and dried with $N_2$ gas. The film was placed into the metal evaporator and a Cr/Au layer (2 nm Cr, 15 nm Au) was added as an overlayer following a previously published procedure (Sorrell, C. D.; Carter, M. C. D.; Serpe, M. J., 2011, Adv. Funct. Mater., 21:425). Prior to any measurements, the etalons were soaked in DI water overnight at 30° C. This was necessary to allow the microgel layer between the Au layers to solvate completely.

Reflectance measurements were conducted using a Red Tide USB650 spectrometer, a LS-1 tungsten light source, and a reflectance probe from Ocean Optics (Dunedin, Fla.). The spectra were recorded using Ocean Optics Spectra Suite Spectroscopy Software at room temperature over a wavelength range of 400-1000 nm. Measurements were conducted by placing the film in a petri dish with water at room temperature. The probe tip was immersed in the water and its distance from the etalon surface adjusted for optimal signal. The probe remained undisturbed between measurements to ensure that all of the spectra were taken in the same manner. The film was moved under the probe and at least three measurements were taken for each film in different areas.

Microscope images of the films were taken using an Olympus IX71 inverted microscope (Markham, Ontario) fitted with a 100x oil-immersion objective, and a 10x eyepiece, differential interference contrast (DIC) optics, and an Andor Technology iXon+camera (Belfast, Ireland). A 1.6× magnification booster was used where specified. Andor SOLIS v4.15.3000.0 software was used to record microscope images of the microgel films. An image of an Edmunds Industrial Optics (Barrington, N.J.) PYSER-SGI scale grating (50×2 microns) was used to determine the scale bars.

Images of the microgel films were taken with a LEO 1430 SEM (Carl Zeiss SMT AG, formerly LEO Electron Microscopy Ltd., Oberkochen, Germany). Samples in the SEM were tilted 80° relative to the source.

Photon Correlation Spectroscopy (PCS) measurements were performed using a Brookhaven Instruments ZetaPlus zeta potential analyzer and ZetaPlus microgel sizing software v.5 (Holtsville, N.Y.). All measurements were taken at 25° C. in 10 mM formate buffer (pH 3.0, 10 mM ionic strength as NaCl). Each hydrodynamic diameter is reported as an average of five 30 s acquisitions and averaged over five measurements per sample.

In our previous studies (Sorrell, C. D.; Carter, M. C. D.; Serpe, M. J., 2011, Adv. Funct. Mater., 21: 425), etalons were made by allowing 775 µL of a 5% (v/v) solution of ~1.5 µm diameter pNIPAm-co-AAc-1 microgels to air dry on a Au coated glass cover slip (2 nm Cr was used as an adhesion layer followed by 15 nm Au). FIG. 10, part a, shows a photograph of the resultant film after coating with a 2 nm Cr/15 nm Au overlayer to make the etalon. FIG. 10, parts b and c show differential interference microscopy (DIC) images of the resultant microgel film in FIG. 10, part a, prior to the Cr/Au overlayer addition. As can be seen, the film's color is visually variable, and the microgel packing density is not consistent from location to location. Additionally, we determined that it was not possible to completely coat a Au substrate with a dense, monolithic layer of microgels by simply increasing the microgel concentration, and air-drying (over the concentration range investigated). These effects are most likely a result of the so-called "coffee-ring effect". Microgels appear concentrated in certain regions of the film, caused by the presence of high capillary flow at drying boundaries. The flow carries and deposits a higher concentration of the microgels to the edge of the drying droplet. As the droplet evaporates, an oscillating pinning/dewetting process takes place at the drying edge, while microgels are simultaneously adhering to the surface in the bulk droplet itself. It is the combination of the coffee ring effect and the native attraction of the microgels to the surface in the bulk droplet that is most likely resulting in the observed inconsistent surface coverage.

Based on the efforts of many groups to understand and manipulate the assembly of colloids onto surfaces from dilute solution, (Denkov, N.; Velev, O.; Kralchevski, P.; Ivanov, I.; Yoshimura, H.; Nagayama, K. Langmuir, 1992, 8, 3183; Deegan, R. D.; Bakajin, O.; Dupont, T. F.; Huber, G.; Nagel, S. R.; Witten, T. A. Nature, 1997, 389, 827; Deegan, R. D.; Bakajin, O.; Dupont, T. F.; Huber, G.; Nagel, S. R.; Witten, T. A. Phys. Rev. E, 2000, 62, 756; Deegan, R. D. Phys. Rev. E, 2000, 61, 475.; Hu, H.; Larson, R. G. J. Phys. Chem. B, 2006, 110, 7090; Kaya, D.; Belyi, V. A.; Muthukumar, M. J. Chem. Phys., 2010, 133, 114905/1.) we hypothesized that modifying the properties of the deposition solution would affect the resultant film structure. Microgel concentration, drying time, surfactant concentration, co-solvent ratios, and pH and ionic strength were all investigated. While the different deposition conditions did yield films with slightly improved surface coverage, no combination of the above solution conditions resulted in the desired jammed microgel layers. However, from the experiments, it was confirmed that drying is critical for making jammed microgel films, i.e., exposing a Au coated surface to a microgel solution for increasing time (without drying) does not result in increased surface coverage. Only by drying can one manipulate the surface coverage. Therefore, we reasoned that to counteract the coffee-ring effect, microgels needed to be highly concentrated and the drying process needed to be continuously disrupted.

To achieve this, we developed the "paint-on" method as detailed in the experimental. Briefly, 40 µL of microgel particles concentrated by centrifugation of a dilute solution of particles at 8400 rct for 30 minutes were spread onto an annealed, clean, Au coated glass substrate and allowed to dry completely. Once completely dry, the film was rinsed copiously with deionized water to remove any microgels that were not directly bound to the Au substrate. The film was then placed into a deionized water bath and allowed to sit overnight at ~30° C. Soaking the film in this manner increases the quality of the resultant etalon, likely a result of possible multilayers breaking up and being removed from the surface, leaving only a jammed monolayer. There is no evidence to suggest that the microgels are moving or migrating on the Au surface during soaking, indicating a very strong microgel-Au bond. We hypothesize that the Au-microgel bond is facilitated not only by weak van der Waals interactions, but also through the free electrons present on the amide N present in NIPAm. These interactions certainly lead to more robust films on Au (and presumably other metal surfaces) than $SiO_2$. Films made by the "paint-on" technique are dense and uniform, with no major defects, as can be seen in FIG. 10, parts d and e. The painted microgel films are also extremely robust: we have soaked painted films in water for up to 48 days with no obvious loss in microgel density or change in film morphology/structure.

Visually, etalons made via the described "paint-on" method are more uniform than etalons fabricated using our previously described drying protocol (Sorrell, C. D.; Carter, M. C. D.; Serpe, M. J., 2011, Adv. Funct. Mater., 21:425). This is a direct result of the increased quality of the microgel coating that serves as the dielectric layer. These painted etalons are of higher spectral quality as well. To quantify the spectral quality of the etalons generated using the two different techniques, we collected reflectance spectra over random regions of the etalons. Spectra for three randomly selected regions of an etalon generated via the "paint-on" technique show all regions displaying reflectance peaks at very similar wavelengths. Spectra for three randomly selected regions of an etalon generated from microgels deposited via the overnight drying method show reflectance spectra much more variable with position on the etalon. Moreover, because some regions do not have the jammed layer of microgels required to make an etalon, no reflectance spectrum is observed in these regions; for the experiment here, only three out of four randomly chosen regions exhibited reflectance spectra.

The uniformity of the etalons made by the "paint-on" technique is further demonstrated by investigating their temperature dependent optical properties and by comparing to etalons made by our previous passive drying method. When compared to etalons made via the drying method, etalons made via the described "paint-on" method exhibit more consistent optical properties over the whole surface area, as evidenced by similar $\lambda_{max}$ values at all temperatures investigated. Additionally, the virtually constant phase transition temperature is independent of the etalon location being probed.

To illustrate the universality of the "paint-on" technique, microgels with varying chemical functionalities and diameters were deposited on Au coated substrates. FIG. 11 shows the resulting materials. In each case the technique produces a jammed, monolithic microgel film, as seen in the DIC images. Furthermore, when a Au overlayer is deposited onto the microgel layer, a high quality etalon is produced, as seen in the photographs in FIG. 11 (insets). FIG. 11, parts a-c, shows etalons generated from microgels with identical chemical composition (in terms of monomer percentages), but differing microgel diameter, (Table 2, below). DIC microscopy images reveal that the resultant microgel films are jammed, and apparently monolithic. Further, the photographs show the concomitant visual color when a Au overlayer is deposited. The reflectance spectra after a Au overlayer is deposited on the microgel layer, shows that each etalon is of high spectral purity, and in each case, a unique spectrum is produced with a varying number of peaks. The number of peaks likely corresponds to different Au mirror spacings, which results from differing microgel diameters. This leads to a change in the Au-Au, or mirror-mirror, spacing.

TABLE 2

Hydrodynamic radii and the standard deviations for the microgels investigated.

| Microgel | Hydrodynamic Diameter ($D_H$), nm |
| --- | --- |
| pNIPAm-co-AAc-1 | 1548 ± 69 |
| pNIPAm-co-AAc-2 | 659 ± 21 |
| pNIPAm-co-AAc-3 | 229 ± 10 |
| pNIPAm-BIS | 671 ± 17 |
| pNIPAm-co-AAm | 653 ± 10 |
| pNIPAm-co-VAA | 602 ± 17 |

FIG. 11, parts d-f, shows etalons created from microgels with different comonomer compositions. Again, it is apparent from the microscopy images that a jammed, monolithic microgel layer is produced irrespective of microgel composition. Furthermore, when a Au overlayer is deposited, visual color is again observed. The spectra for the respective films collected over random regions of the etalon illustrate the high quality of the microgel layer, and of the resulting etalon. This data shows that microgel composition and/or size is unimportant for generating quality films using the described painting protocol.

FIG. 11, parts g and h, shows a photograph of an etalon generated on a Au coated flexible surface (a transparency) and FIG. 11, part i, shows the microscopy image illustrating the resultant monolithic microgel film. Evidently, the underlying substrate is not important for the technique to be effective; the only requirement is that the substrate be coated with Au. The microgel film deposited on the Au coated transparency produces a high quality etalon, and continues to be even when the etalon is bent. The 'bent' spectrum shows that the red curve closely matches the spectra obtained on other regions of the unbent etalon. However, because of the nature of the measurement, we cannot be sure of how bending the etalon shifts the reflectance spectrum. This experiment was performed merely to prove that our materials behave as etalons even on a bent, flexible substrate.

While microgel based etalons are important for future investigations specific to our lab, the fact that jammed, monolithic microgel films can be deposited on Au coated substrates, with extreme ease despite the size or chemical functionality of the microgels or the nature of the substrate, is of broader interest and applicability. We went on to show that the technique could be extended to coat Si surfaces with microgels, which also results in etalons when a Au overlayer is deposited on top. While this did generate an etalon, the microgel coating is not as robust when compared to those generated on Au coated substrates.

We have developed a "paint-on" technique that allows for the reproducible generation of j ammed, monolithic microgel layers on Au coated substrates. The technique appears to be universal; microgels of various chemical functionality and size can be deposited on substrates, so long as they are coated with Au. The quality of the microgel coating is evidenced by visual purity, DIC microscopy and the high spectral purity of the etalons generated after coating the microgel layer with Au. Reflectance spectra were collected over different regions of etalons generated from the "paint-on" method; they show highly consistent peak positions, which was not the case for etalons generated using our previously presented drying protocol. The "paint-on" technique is advantageous because of its ease, simplicity, and apparent universality. We are confident that this technique could easily be scaled up to coat Au coated substrates with larger surface areas or applied to a variety of metal-coated surfaces. We also aim to extend the technique to coat Au coated substrates with other types of polymers and materials. As we develop more optically pure and structurally complex etalons, we anticipate being able to monitor the presence of analytes and detect stimuli with the unaided eye. New 1—Sorrell, C. D., et al., 2012, Glucose Sensitive Poly (N-Isopropylacrylamide) Microgel Based Etalons, Anal. Bioanal. Chem. 402:2385-2393.

In this example, we disclose the utility of microgel based etalons for sensing applications. Using APBA-functionalized microgel etalons, we are able to detect glucose both visually and spectrally. Spectrally, the etalon's reflectance peaks red-shift in response to glucose addition, yielding a visible color change. APBA is not specific for glucose, as it can bind to other diols non-specifically, the purpose of this manuscript is to demonstrate that biologically relevant molecules (glucose) can enter the etalon, interact with the APBA modified microgels, and afford a colorimetric and spectral response. Dispersed APBA functionalized microgels are known to swell in the presence of glucose, but it is unclear how they respond in devices that are able to produce a readout signal—this example shows that the APBA microgels function in our devices as expected from their solution behavior and also shows that confined, functional microgels can interact with their environment for sensing applications.

N-isopropylacrylamide was purchased from TCI (Portland, Oreg.) and purified by recrystallization from hexanes (ACS reagent grade, EMD, Gibbstown, N.J.) prior to use. N,N'-methylenebisacrylamide (BIS) (99%), acrylic acid (AAc) (99%), ammonium persulfate (APS) (98+%), α-D-glucose (ACS reagent), and 3-aminophenylboronic acid hydrochloride (APBA) (98%) were obtained from Sigma-Aldrich (Oakville, Ontario, Milwaukee, Wis., and St. Louis, Mo.) and were used as received. Sodium chloride and sodium phosphate monobasic were obtained from Fisher (Ottawa, Ontario) and used as received. Sodium bicarbonate ($NaHCO_3$) and sodium carbonate ($Na_2CO_3$) were obtained from Caledon Laboratories Ltd. (Rockville, Ontario) and were used as received. 1-Ethyl-3-(3-dimethylaminopropyl) carbodiimide hydrochloride (EDC) and BupH 2-(N-Morpholino)ethanesulfonic acid (MES) Buffered Saline packets were obtained from Pierce through Thermo Scientific (Rockford, Ill.) and were used as received or according to the package instructions. All deionized water was filtered to have a resistivity of 18.2 MΩ·cm and was obtained from a Milli-Q Plus system from Millipore (Billerica, Mass.). Anhydrous ethanol was obtained from Commercial Alcohols (Brampton, Ontario). Glass cover slips were 25×25 mm and obtained from Fisher Scientific (Ottawa, Ontario). Cr and Au were 99.999% and obtained from ESPI (Ashland, Oreg.). Au annealing was performed in a Thermolyne muffle furnace from Thermo Fisher Scientific (Ottawa, Ontario). Photographs of the films were taken with a Pentax K2000 DSLR camera fitted with a SMC Pentax-DA 1:2.8 35-mm rectilinear macro lens. Image processing of the photographs was performed using Picasa 3 (Google, Menlo Park, Calif.).

Microgels and etalons were prepared using other previously described techniques (Serpe, M. J.; Jones, C. D.; Lyon, L. A., 2003, Langmuir, 19: 8759; Jones, C. D.; Lyon, L. A., 2000, Macromolecules, 33: 8301). Microgels of three different diameters were used for the current study, and they will be annotated as pNIPAm-co-AAc-1 (large diameter), pNIPAm-co-AAc-2 (medium diameter), and pNIPAm-co-AAc-3 (small diameter) throughout the text. The microgels had a hydrodynamic diameter of 1547.8 nm (±15.8 nm), 659.3 nm (±9.9 nm), and 229.0 nm (±4.6 nm), respectively, as measured by photon correlation spectroscopy. Specific details for the microgel syntheses and characterization can be found below.

The pNIPAm-co-AAc-1 large diameter microgels were synthesized following a previously published procedure (Meng Z, Smith MH, Lyon LA, 2009, Temperature-programmed synthesis of micron-sized multi-responsive microgels, Colloid Polym Sci, 287:277-285). N-isopropylacrylamide (NIPAm, 17.0 mmol) and N,N'-methylenebisacrylamide (BIS, 1.00 mmol) were added to 100 mL of deionized water in a small beaker and stirred. Once dissolved, the solution was filtered through a 0.2 μm filter in a 3-neck flask. The beaker was rinsed with 25 mL of deionized water and the rinsate was filtered into the flask. The flask was fitted with a condenser, a nitrogen inlet, and a temperature probe to provide heating via a feedback-loop controlled hotplate (Torrey Pines Scientific, Carlsbad, Calif.). The flask was heated in an oil bath to 45° C. while the solution was allowed to stir and purge with N2 over about 1.5 hours. Then acrylic acid (AAc, 2.00 mmol) was added in one aliquot. The reaction was then initiated with a 0.078 M aqueous solution of ammonium persulfate (APS, 5 mL). After initiation, the reaction solution was then heated at a rate of 30° C./hour to 65° C. and the reaction was allowed to proceed overnight under a blanket of nitrogen. The resulting suspension was allowed to cool to room temperature, and then it was filtered through a plug of glass wool to remove any coagulum formed during the reaction. The microgel solution was then distributed into centrifuge tubes and purified via centrifugation at ~8300 rcf to form a pellet, followed by removal of the supernatant and resuspension with deionized water, 6×. The cleaned microgels were recombined and stored in a brown glass jar. Microgels in pH 3 10 mM formate buffer (10 mM I.S.) had a diameter of 1547.8 nm (±15.8 nm).

The pNIPAm-co-AAc-2 medium diameter microgels were synthesized following a previously published procedure (Serpe M J, Jones C D, Lyon L A, 2003, Layer-by-Layer Deposition of Thermoresponsive Microgel Thin Films., Langmuir, 19:8759-8764). A 3-neck flask was fitted with a reflux condenser, nitrogen inlet, and temperature probe (as above), and charged with a solution of NIPAm (11.9 mmol) and BIS (0.703 mmol) in 99 mL deionized water, previously filtered through a 0.2 μm filter. The solution was purged with N2 and allowed to heat to 70° C. over ~1 hour. AAc (1.43 mmol) was added to the heated reaction mixture in one aliquot. The reaction was then initiated with a solution of APS (0.2 mmol) in 1 mL of deionized water. The reaction was and allowed to proceed at 70° C. for 4 hours under a blanket of nitrogen. The resulting suspension was allowed to cool overnight, and then it was filtered through a Whatman #1 paper filter to remove any large aggregates. The microgel solution was then distributed into centrifuge tubes and purified via centrifugation at ~8300 rcf to form a pellet, followed by removal of the supernatant and resuspension with deionized water, 6×. The cleaned microgels were recombined and stored in a brown glass jar. Microgels in pH 3 10 mM formate buffer (10 mM I.S.) had a nominal diameter of 659.3 nm (±9.9 nm).

The pNIPAm-co-AAc-3 small diameter microgels were synthesized following a previously published procedure (Jones C D, Lyon L A, 2000, Synthesis and Characterization of Multiresponsive Core-Shell Microgels, Macromolecules, 33:8301-8306). A 3-neck flask was fitted with a reflux condenser, nitrogen inlet, and temperature probe (as above), and charged with a solution of NIPAm (11.1 mmol), BIS (0.652 mmol), and sodium dodecyl sulfate (SDS, 0.2 mmol)

in 190 mL deionized water, previously filtered through a 0.2 µm filter. The solution was purged with N2 and allowed to heat to 70° C. over ~1 hour. AAc (1.30 mmol) was added to the heated reaction mixture in one aliquot. The reaction was then initiated with a solution of APS (0.3 mmol) in 10 mL of deionized water. The reaction was and allowed to proceed at 70° C. for 4 hours under a blanket of nitrogen. The resulting suspension was allowed to cool overnight, and then it was filtered through a Whatman #1 paper filter to remove any large aggregates. Approximately half of the microgel solution was then distributed into rehydrated dialysis tubing (12-14k nominal MWCO, 25 mm flat width, Fisherbrand Regenerated Cellulose, Nepan, ON) for purification. The tubes were placed into two 2 L beakers with deionized water and a stir bar for two weeks and the water was replaced 2× daily. The cleaned microgels were recombined and stored in a brown glass jar. Microgels in pH 3 10 mM formate buffer (10 mM I.S.) had a diameter of 229.0 nm (±4.6 nm).

The pNIPAm-BIS microgels were synthesized in the same manner as the pNIPAm-co-AAc-2 microgels. A 3-neck flask was fitted with a reflux condenser, nitrogen inlet, and temperature probe (as above), and charged with a solution of NIPAm (66.5 mmol) and BIS (3.51 mmol) in 495 mL deionized water, previously filtered through a 0.2 µm filter. The solution was purged with N2 and allowed to heat to 70° C. over ~1 hour. The reaction was then initiated with a solution of APS (1.0 mmol) in 5 mL of deionized water. The reaction was and allowed to proceed at 70° C. for 4 hours under a blanket of nitrogen. The resulting suspension was allowed to cool overnight, and then it was filtered through a Whatman #1 paper filter to remove any large aggregates. The microgel solution was then distributed into centrifuge tubes and purified via centrifugation at ~8300 rcf to form a pellet, followed by removal of the supernatant and resuspension with deionized water, 6×. The cleaned microgels were recombined and stored in plastic centrifuge tubes in the dark. Microgels in pH 3 10 mM formate buffer (10 mM I.S.) had a nominal diameter of 670.6 nm (±8.0 nm).

PCS measurements were performed using a Brookhaven Instruments ZetaPlus zeta potential analyzer and ZetaPlus particle sizing software v.5 (Holtsville, N.Y.). All measurements were taken at 25° C. in 10 mM formate buffer (pH 3, 10 mM ionic strength due to NaCl). Each hydrodynamic diameter is reported as an average of five 30 s acquisitions and averaged over five measurements per sample. Etalons were fabricated following a previously published procedure (Sorrell C D, Carter M C D, Serpe M J, 2011, Color Tunable Poly (N-Isopropylacrylamide)-co-Acrylic Acid Microgel-Au Hybrid Assemblies, Adv Funct Mater 21:425-433; Sorrell C D, Carter M C D, Serpe M J, 2011, A "Paint-On" Protocol for the Facile Assembly of Uniform Microgel Coatings for Color Tunable Etalon Fabrication, ACS Appl Mater Interfaces 3:1140-1147; Sorrell C D, Serpe M J, 2011, Reflection order selectivity of color-tunable poly (N-isopropylacrylamide) microgel based etalons, Adv Mater 23: 4088-4092). To fabricate the Au coated coverslips (etalon underlayer), 2 nm Cr and 15 nm of Au was added to a 25×25 mm ethanol rinsed and N2 gas dried glass coverslip (Fisher's Finest, Ottawa, ON) at a rate of 1 Å s−1, and 0.1 Å s−1, respectively (Ton International Inc., thermal evaporation system, Model THEUPG, New Windsor, N.Y.). The Cr/Au substrates were annealed at 250° C. for 3 h (Thermolyne muffle furnace, Ottawa, ON) and cooled to room temperature prior to microgel film deposition.

Approximately 5-10 mL of microgel solution was centrifuged at ~8300 rcf to form a pellet. The supernatant was removed and discarded, and the pellet was vortexed to loosen and homogenize the particles in the remaining solvent. A 40 uL aliquot of concentrated microgels were spread onto an annealed 25mm×25 mm Au-coated glass coverslip. The film was allowed to dry on a 30° C. hotplate for 30 minutes before the excess microgels were rinsed with deionized water. The samples were soaked overnight at 30° C. in a deionized water bath. The samples were then rinsed with deionized water, dried with N2, and functionalized as described in the main text. After rinsing and soaking to remove unreacted reagents, another Au overlayer (2 nm Cr for adhesion, followed by 15 nm Au) was added. The completed device was soaked overnight in deionized water at 30° C.

Functionalization of microgels with 3-aminophenylboronic acid (APBA) was performed on a set of microgel films on gold similar to previously published procedures (Zhang Y, Guan Y, Zhou S, 2006, Synthesis and Volume Phase Transitions of Glucose-Senstive Microgels,Biomacromolecules, 7:3196-3201; Hoare T, Pelton R, 2007, Engineering Glucose Swelling Responses in Poly(N-Isopropylacrylamide)-Based Microgels, Macromolecules, 40:670-678). All reagents were used in excess to ensure complete conversion of the acrylic acid moieties in the microgels to APBA-functional groups.

Briefly, pNIPAm-co-AAc microgel thin films (for the three sizes of microgels) were painted onto a 15 nm Au gold-coated glass cover slip (2 nm Cr adhesion layer) to create a homogeneous, monolithic film. The films were soaked overnight in deionized water to remove any non-specifically adsorbed microgels. The microgel films were placed in pH 4.7 MES buffered saline (Pierce, prepared according to the packet instructions) and 9 mg APBA was added to the buffer. The solution and sample were allowed to mix for 1 hour on a Gyratory Water Bath Shaker G76 (Brunswick Scientific Co., New Brunswick, N.J.). To the mixture and sample, 20 mg EDC was added to the buffered APBA solution and sample. The mixture was swirled to dissolve the EDC, and the sample was placed into the refrigerator for 5 hours. An additional 4.5 mg aliquot of APBA was added per sample to the solution and the mixture was allowed to mix on a gyrating shaker table for 30 minutes. Then an additional 20 mg per sample of EDC was added and dissolved, and the reaction was allowed to go overnight at 4° C.

Control samples were made as above using pNIPAm-co-AAc microgel films treated with either APBA only or EDC only in pH 4.7 buffer. A set of double controls was made as above using NIPAm-BIS microgels without an AAc comonomer by adding APBA and EDC, as well as APBA only and EDC only.

All samples were rinsed with deionized water and soaked in pH 7.2 10 mM PBS buffer (with 150 mM ionic strength from NaCl) for several hours to remove any unreacted reagents. The samples were rinsed and dried and placed into a gold evaporation apparatus (Torr International Inc. model THEUPG thermal evaporation system, New Windsor, N.Y.) and 2 nm Cr (adhesion layer) and 5 nm Au was evaporated onto the functionalized films at a rate of 1 Å s$^{-1}$, and 0.2 Å s$^{-1}$, respectively. The completed etalons were soaked in deionized H$_2$O. Prior to analysis, the etalons were rinsed and placed in pH 9 carbonate buffer for storage.

A 5 mM pH 9 carbonate buffer was prepared by dissolving 0.76 g NaHCO$_3$ and 0.11 g Na$_2$CO$_3$ in 2 L deionized H$_2$O in a volumetric flask. The resulting solution measured pH 9.3. To prepare the glucose buffer, 3.0 g of α-D-glucose was dissolved in 500 mL of 5 mM pH 9 carbonate buffer to give a 6 mg/mL glucose solution. The final pH was 9.3.

Each sample was measured for thermoresponsivity in 24 mL of pH 9 buffer in a temperature controlled chamber fitted with a UV/vis reflectance probe. The sample and buffer were cooled to 15° C. and the temperature was changed manually by increasing in increments of 3° C. up to 39° C. The temperature was allowed to stabilize for 5 minutes at each temperature before a spectrum was recorded.

After the initial temperature study, the sample was cooled back to 15° C. Approximately 12 mL of the pH 9 carbonate buffer was removed from the temperature controlled chamber using a glass syringe and was replaced with a cooled solution of 6 mg/mL glucose in pH 9 carbonate buffer, resulting in a final concentration of 3 mg/mL glucose in the chamber. Once the glucose was introduced, a spectrum was recorded every 1 minute using Ocean Optics Spectra Suite Spectroscopy Software (Dunedin, Fla.) for 2 hours. Following equilibration with glucose, the temperature responsivity was measured again in the same manner as above keeping the sample in the glucose solution.

In-liquid height analysis for a pNIPAm-co-AAc-2 microgel etalon in 5 mM carbonate buffer, pH 9 and 3 mg/mL glucose in pH 9 buffer solution was performed using the APBA-functionalized and the APBA exposed control samples used in this study. The images were acquired using an Asylum Research MFP 3D AFM (Santa Barbara, Calif.). Images were acquired over a 50 µm×50 µm area using a scan rate of 0.45 Hz, using 512 scan points and lines. The tips were Olympus TR800PSA with a resonant frequency of 24 kHz. An image was taken using a sessile drop method first in pH 9 carbonate buffer at ~24° C. The samples were treated with 3 mg/mL glucose solution for at least 2 hours in a cooler with ice to approximate the binding conditions used in the experiments above. Then the samples were imaged in a sessile drop of 3 mg/mL glucose in pH 9 buffer at an ambient chamber temperature of ~24° C. For this analysis, a line was scratched into the sample using a new razor blade and the scratch was imaged. The height was determined using the software by taking 100-line blocks and measuring the height on a line trace. Four 100-line blocks were measured and averaged to get an average height and standard deviation for each image.

Functionalization of microgels in solution can be difficult due to aggregation and destabilization of the colloid as a result of a change in the surface charge density, and a concomitant change in the interaction potential of the microgels. Therefore, functionalization of the microgels for these studies was performed on the painted films before Au overlayer addition. First, the microgels were painted onto a 15 nm Au (with 2 nm Cr adhesion layer) base layer on glass and soaked overnight to remove any non-specifically adsorbed microgels. The microgel films were then subjected to functionalization in pH 4.7 MES buffer with EDC and APBA (FIG. 19, part a). Etalon fabrication was completed by adding a 5 nm Au overlayer to the functionalized films (with 2 nm Cr adhesion layer). After rehydrating the films in water and then in 5 mM pH 9 carbonate buffer, the devices were ready for analysis.

The analysis of the glucose sensitive materials was performed in 5 mM pH 9 carbonate buffer. In a basic buffer the boronic acid moieties on the APBA ($pK_a$=8.2) were hydroxylated such that the boron possesses a negative charge (FIG. 19). The binding for diols, like glucose, is favored for boronic acids in the charged state. As glucose binds, more boronic acid groups must convert to the charged state in order to maintain the equilibrium, which effective lowers the $pK_a$. As more boron atoms become charged, more glucose can bind until equilibrium is reached. In the presence of glucose, the bound state is preferred promoting more hydroxylation of the boron atoms into a charged form, leading to an increase in the Coulombic repulsion inside the microgel, which results in a swelling response. In the etalons this will be observed as a red shift, according to equation 3. It is known that the change in the distance between the Au is more important for tuning of the etalon color than changes in the refractive index, n. We are able to measure the binding of glucose directly using our etalons and observing the spectral shift that results from microgel swelling. We exposed the etalons to a 3 mg/mL solution of glucose in pH 9 carbonate buffer and observe changes in peak position in the etalon's spectrum as a function time. For pNIPAm-co-AAc-2 microgel etalons functionalized with APBA, we see a 134 nm spectral shift in the most red-shifted peak starting at 856 nm and ending at 990 nm over the course of 2 hours. When the peak position is plotted as a function of time, it becomes apparent that the majority of the spectral shift is observed within 30 minutes of glucose introduction, with an eventual leveling off as the boronic acid groups bind and reach an equilibrium with the available glucose. This observation is similar to other known hydrogel sensing devices using boronic acid binding of glucose. The controls that were exposed during fabrication to either APBA only or EDC only showed only minimal changes in the spectrum or peak position after the addition of glucose. A double-control was also performed using pNIPAm-BIS microgels that did not have any acrylic acid as a co-monomer. These microgels were treated in the same way as all of the samples containing acrylic acid using APBA and EDC. These microgels continued to show responsivity to temperature even in the pH 9 carbonate buffer, but they also did not exhibit any shifts in the VPTT of the film nor responsivity after exposure glucose.

Prior to binding with glucose we measured the thermoresponsivity of the APBA modified pNIPAm-co-AAc-2 microgel etalons in 5 mM pH 9 carbonate buffer. We measured the etalon's spectrum every 3° C. between 15° C. and 39° C. When the most red-shifted peak position is plotted as a function of temperature we see that the behavior mimics previously-studied microgels in solution. Native pNIPAm microgels in solution exhibit a VPTT of ~32° C. The APBA etalons, however, exhibit an initial VPTT of ~18° C. with a total shift of ~400 nm in response to temperature. When Zhou and co-workers (Zhang Y, Guan Y, Zhou S, 2006, Synthesis and Volume Phase Transitions of Glucose-Senstive Microgels, Biomacromolecules, 7:3196-320) studied APBA functionalized microgels in solution they reported a depressed VPTT of 17° C. This comparison is important to make, as it shows that microgel confinement does not affect their function. Zhou and co-workers attributed this to the increased hydrophobicity imparted to the microgels as a result of the APBA functional group. After exposure of the APBA-functionalized etalon to 3 mg/mL glucose solution in pH 9 carbonate buffer, the etalon's spectrum red shifts 134 nm. If the wavelength position of that shifted peak is again monitored as a function of temperature, an increase in the VPTT to 24° C. is observed. The VPTT for glucose-bound APBA functionalized microgels in solution as reported by Zhou and co-workers is also 24° C. In our case we see a total 6° C. shift in the VPTT, which is similar to the 7° C. shift seen by Zhou, as well as the 4° C. shift reported by Hoare and Pelton for APBA functionalized microgels in solution (Hoare T, Pelton R, 2007, Engineering Glucose Swelling Responses in Poly(N-Isopropylacrylamide)-Based Microgels, Macromolecules, 40:670-678). The shift of the VPTT is attributed to an increase in the charge density inside the particles causing Coulombic repulsion. The controls exposed to APBA only or EDC only do not exhibit any thermoresponsivity because the AAc groups have not been modified in any way. At pH 9, the AAc groups are well above their $pK_a$ and will all be negatively charged. In such cases, the Coulombic repulsion of the —COO⁻ groups inside the gel will be enough to suppress the thermoresponsivity. As mentioned above, the position of the control peaks changes minimally after glucose exposure. Therefore, after glucose exposure the response to temperature is still suppressed by the Coulombic repulsion of the AAc groups in the microgels.

Etalons made with larger and smaller microgels (pNIPAm-co-AAc-1 and pNIPAm-co-AAc-3, respectively) show a comparable response by: a) exhibiting a red shift in the spectrum upon the addition of glucose, and b) exhibiting a shift in the VPTT before and after glucose addition. The magnitude of the response of these etalons to glucose is very similar to the medium diameter pNIPAm-co-AAc-2 microgel etalons. Important to note is that all of the APBA-functionalized devices exhibit the majority of their response within 30 minutes of glucose introduction. This indicates that the binding is more affected by the binding equilibrium of the glucose with the boronic acid, rather than the incorporation of the analyte into the device. While it is the case that the majority of the response exhibited by each etalon occurs within 30 minutes of glucose introduction, the large diameter microgels do exhibit slower response kinetics, shifting an additional 35 nm overnight after the initial 2 hours. In comparison, the medium and small microgels do not show any additional spectral shift after overnight incubation. The most notable difference between the etalons made from microgels of different size is that each of them produce spectra with different numbers of peaks where the smallest microgels giving a single reflectance peak, and the largest gives five peaks. As expected, the medium diameter pNIPam-co-AAc-2 microgels give an etalon that exhibits an intermediate number of spectral peaks (FIG. 19, part a). We have shown previously that the spectral properties can be tuned by changing the size and stiffness of the microgels in order to produce an etalon with a single reflectance color, both spectrally and visually. These and other parameters, such as responsivity to specific analytes, will be crucial in directing design of these materials for real POC usage.

When the etalons are analyzed in the same manner as the pNIPAm-co-AAc-2 microgel etalons, the large diameter pNIPAm-co-AAc-1 microgels show an overall 150 nm shift in the spectrum due to glucose binding inside the film. Similarly, the small diameter microgel etalons show a 110 nm shift. For the pNIPAm-co-AAc-1 microgel etalons, the VPTT of the APBA functionalized films is 18° C., but shifts to 27° C. after incubation overnight in 3 mg/mL glucose. The etalons made with the small diameter microgels, pNIPAm-co-AAc-3, show a similar response with a VPTT of 20° C. before glucose addition that shifts to 26° C. after incubation with glucose. This is important because it shows that changing the microgel does not change the expected response, and indicates that the spectral and visual color properties can be tuned without losing sensitivity.

Atomic force microscopy (AFM) imaging, and subsequent height analysis, shows that the APBA-functionalized pNIPAm-co-AAc-2 etalons exhibit a total change in d of (+)43 nm after the addition of glucose. At an ambient AFM chamber temperature of 24° C., the etalons have a d of 340 nm (±9 nm). After incubating the etalon with 3 mg/mL glucose in pH 9 carbonate buffer for 2 hours the total thickness increased to 383 nm (±5 nm). If we assume that we are looking at a first order peak for these materials, we can use equation 3 to calculate the expected total change in d that should yield the observed Δλ. Assuming a refractive index of 1.4, and a first order peak, the Δλ should be (+)70 nm at 24° C. This calculated value closely matches the actual change in d, indicating that our etalon functions as expected. The control exposed to APBA only during fabrication did not show a significant change in thickness by AFM before and after glucose addition, as expected. The APBA only etalon was 777 nm (±10 nm) thick before reaction with glucose and 787 nm (±27 nm) thick after reaction with glucose Ultimately, we hope to use these materials as optical readout sensor devices for POC diagnostics, similar to a pregnancy test or a glucose monitor. In FIG. 20 we show photographs of the etalons used in the spectral experiments as a proof of concept. In FIG. 20, parts a and b, are pictures of the APBA functionalized pNIPAm-co-AAc-2 microgel etalon before and after glucose addition, respectively. While the color change is subtle, it is visibly detectable, and the entire etalon exhibits a complete color reversal going from mostly green at pH 9 as shown in FIG. 20, part a, to mostly red in a 3 mg/mL glucose solution as shown in FIG. 20, part b. The controls in FIG. 20, parts c-f, do not show any significant differences before and after glucose addition further indicating that the addition of glucose does not change their properties significantly enough to elicit a colorimetric response.

We have demonstrated that microgel etalons are good platforms for sensing applications by using them to spectrally and visually detect glucose in aqueous solution. Functionalization of microgels at an interface is a reasonable alternative to functionalization of microgels in solution, which may result in irreversible aggregation. The surface-functionalized microgels exhibit similar behavior to that seen by previous investigators for microgels in solution. In response to glucose, APBA functionalized microgel etalons exhibit 110-150 nm red-shift in response to a 3 mg/mL glucose solution in 5 mM pH 9 carbonate buffer at 15° C. Additionally, before binding with glucose the etalons exhibit a VPTT of 18-20° C., which shifts to 24-26° C. after glucose addition. Etalons with microgels of different sizes give similar responses, the most marked difference being the different numbers of spectral peaks exhibited by each. We further demonstrated that the visual color shift of the device is significant enough to show a clear change in color from green to red before and after the addition of glucose, respectively. These experiments clearly demonstrate microgels etalons' utility for future sensing applications. While glucose sensitive microgels are known, their glucose response needs to be determined via light scattering intensity changes or diameter changes measured via photon correlation spectroscopy. Using the device presented here, their response can simply be read out visually and spectrally if needed. It should also be pointed out that the microgels themselves are thermoresponsive, therefore the material's color can be significantly influenced by temperature. For POC applications, this is a concern.

Based on the properties of the materials tested and for which results are provided, it may be predicted that gel assemblies made of other materials may be formed in like manner and yield like results. The examples provided here are predicted to work based on the results provided here, and the similar properties of stimulus responsive materials to the tested materials.

Thus, the polymeric gel layer may comprise any of the following materials and combinations of them.

oligoethyleneglycol methacrylate-T and pH, O
2-dimethylaminoethyl methacrylate-T and pH, O
2-oxazoline-T, N and O
hydroxypropyl acrylate-T, O
2-2(methoxyethoxy)ethylmethacrylate-T, O
NIPAm-T-N
hydroxypropyl cellulose-T, O
vinylcaprolactone-T, O
(1-hydroxymethyl)propyl methacrylamide, T, N, O
N,N'-diethylacrylamide, T, N, O
hexafluorobutyl methacrylate, T, O, F
propylene oxide/glycol, T, O
2-(methacryloyloxy)ethyl phosphoryl choline-E, T, O, N, P
Spiropyran, pH, L, N, O
azobenzene, L, N
spirooxazine, pH, L, N, O
naphthopyran, L, O
Cinnamate, L, O
ethyleneamine, pH, IS, N
4-vinylbenzoate, pH, IS, O
chitosan, pH, IS, O
acrylic acid, pH, IS, O
2-dimethyl aminoethyl methacrylate, pH, IS, N, O
diethyl aminoethyl methacrylate, pH, IS, N, O
propylacrylic acid, pH, IS, O
vinylpyridine, pH, IS, N
2-(diisopropylamino)ethylmethacrylate, pH, IS, N, O
methacrylic acid, pH, IS, O
glutamic acid, pH, IS, N, O
vinyl imidazole, pH, IS, N
allylamine, pH, IS, N
alginate, pH, IS, O
chondroitin, pH, IS, O
hyaluronic acid, pH, IS, O
2-chloroacrylic acid, pH, IS, O, Cl
saccharides, weak acids and bases, pH, IS
where pH=pH sensitive,T=temperature sensitive, IS=ionic strength sensitive, L=light or photo sensitive, E=electrosensitive and O=oxygen containing, N=nitrogen containing, F=fluorine containing, Cl=chlorine containing, and P=phosphorus containing Polymers may be made magnetosensitive by inclusion of magnetic materials.

The polymers disclosed here are expected to work because they are all hydrophilic polymers, which can be crosslinked to give hydrogels and microgels. These materials can be immobilized between Au (or any metal) layer(s), just like the disclosed pNIPAm based system. The polymers can be swollen with solvent, and change volume in response to the indicated stimuli, therefore changing the color of the etalon. These should all stick to the metal because they have elements with free electron pairs.

In some embodiments, the polymer may comprise any polymer with hydrophilic groups, such as acrylamides, acrylates, silicones, ethylene oxides, ethylene glycols, poly amines, poly ethers, and charged polymers. Each metal layer may be formed of any metal such as Fe, Ni, Ag, Au, Al, Ti, Cu, Cr and need not be the same metal on either side of the gel, and each layer may comprise more than one metal. Advantages of the gel assembly and hydrogel etalon may include, depending on the embodiment: Easy, simple fabrication; Thermoresponsive in some embodiments; Allows functionalization to respond to various stimuli (other than temperature), for example biomolecules; Has a wide colour range (from near-IR to UV); this makes it very useful as a colorimetric sensor with a visual readout in order to avoid costly spectrometers; this is mostly achieved from a changing mirror-to-mirror distance though a change in the index of refraction also contributes.

Some of the other aspects include the following:

As the spreading technique gives better control over the film uniformity, this makes it easier to control release of a drug that is loaded into the polymer gel. For example, gold may be deposited on top of the drug-loaded hydrogel to control drug release, for use for example in implantable devices.

In the example of controlled drug release, a multilayer structure of polymeric gel layers and intervening metal layers formed by repetitive units of the gel assembly may be formed in which drug-loaded hydrogel is sandwiched between consecutive layers of gold. This would allow the release of a different drug after one drug is exhausted and could be useful to avoid bacterial resistance in the case of antibiotic drugs.

The etalon can be used as a tunable filter—for example, by heating it up, one can decrease the wavelength of the light that will be reflected; this is useful as filters for fluorescent microscopes so as to avoid the need to switch to a different filter for a different wavelength used to excite a different fluorophore.

The etalon may be fabricated such that there is only one reflectance peak in the visible spectrum. This spectral purity is useful in colorimetric sensors with a visual readout.

What is claimed is:

1. A gel assembly comprising a polymeric gel layer between metal layers in which the polymeric gel layer is formed as a colloidal gel comprising packed particles, the particles having an unstressed diameter and as packed particles having a center to center particle distance that is smaller than the unstressed diameter.

2. A gel assembly comprising a polymeric gel layer between metal layers in which the polymeric gel layer is loaded with drug.

3. A gel assembly comprising a polymeric gel layer between metal layers incorporated into a microbalance.

* * * * *